United States Patent [19]
Potash et al.

[11] Patent Number: 6,025,182
[45] Date of Patent: Feb. 15, 2000

[54] METHOD FOR PRODUCING A VIRUS FROM AN AFRICAN GREEN MONKEY KIDNEY CELL LINE

[75] Inventors: Louis Potash; Robert M. Chanock, both of Bethesda; Robert H. Purcell, Boyds; Albert Z. Kapikian, Rockville, all of Md.

[73] Assignees: Dyncorp, Reston, Va.; National Institutes of Health, Bethesda, Md.

[21] Appl. No.: 09/048,308

[22] Filed: Mar. 26, 1998

Related U.S. Application Data

[62] Division of application No. 08/790,598, Jan. 29, 1997, which is a division of application No. 08/351,079, Nov. 30, 1994, Pat. No. 5,646,033.

[51] Int. Cl.⁷ ........................................... C12N 7/02
[52] U.S. Cl. ............................................... 435/239
[58] Field of Search ..................... 435/239, 237, 435/235.1

[56] References Cited

U.S. PATENT DOCUMENTS

| | | | |
|---|---|---|---|
| 4,040,905 | 8/1977 | Petricciani et al. | 435/364 |
| 4,571,385 | 2/1986 | Greenberg et al. | 435/456 |
| 4,783,407 | 11/1988 | Provost et al. | 435/235.1 |
| 5,610,049 | 3/1997 | Clark | 435/235.1 |

OTHER PUBLICATIONS

Journal of General Virology, vol. 57, issued 1981, Lee et al., "Serial Propagation of Astrovirus in Tissue Culture with the Aid of Trypsin", pp. 421–424.

Abstracts of the Annual Meeting of the American Society for Microbiology, 23rd Annual Meeting, issued Mar. 1983, Price et al, "The Use of Serially Propagated Monkey Kidney Cell Cultures for the Preparation of High–Titered Hemagglutinin and/or Complement–Fixing Antigens of the Human Parainfluenza Viruses–Type 1, 2 and 3", p. 299, column 2, abstract T22.

Biologicals, vol. 23, No. 3, issued Sep. 1995, Horaud, "Viral Vaccines and Residual Cellular DNA", pp. 225–228, see p. 227, column 1.

Abstract Annual Meeting Am. Soc. Microbiol., 1983 p. 299, Price et al, Abstract T22.

*Primary Examiner*—Terry McKelvey
*Attorney, Agent, or Firm*—Burns, Doane, Swecker & Mathis, L.L.P.

[57] ABSTRACT

A method for producing novel African Green Monkey Kidney (AGMK) cell lines is taught. These cell lines which are free of viable adventitious microbial agents are useful as substrates for viruses and for the preparation of viral vaccines.

8 Claims, 3 Drawing Sheets

```
                    p5A  - L#4098 = MWCB
                           |
                           |--------------------------------------|
                           |                                      |
                    p6A  - L#4156                            L#4664
                           |                                      |
                    p7A  - L#4214                            L#4718
                           |                                      |
                    p8A  - L#4267                            L#4775
                           |                                      |
                    p9A  - L#4300                            L#4900
                           |                                      |
                    p10A - L#4360                            L#5014
                           |                                      |
        |------------------------------------------------|        |
 p11A - L#4474                                      L#4571   L#5096
        |                                                |        |
 p12A - L#4521                                      L#4653   L#5163
        |                                                |        |
 p13A - L#4569                                      L#4744   L#5187
        |                                        |--------|       |
 p14A - L#4608                            L#4820    L#4779   L#5202
        |                                                |        |
 p15A - L#4626                                      L#4847   L#5231
        |-------|--------------|                  |-------|       |
 p16A - L#4654  L#4707         L#4708        L#4883  L#4867   L#5259
        |        |------|       |------|        |        |        |
 p17A - L#4706  L#4725  L#4742/3   L#4755   L#4788   L#4918  L#4889   L#5328
                                    |
                           p18A  - L#4819
                                    |
                           p19A  - L#4843
                                    |
                           p20A  - L#4888
```

FIG. 2

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CCTCAGAGCT GCATAAAAGC AGAT                      24

(2) INFORMATION FOR SEQ ID NO:2:

-continued

```
     (i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

TCACTCAAGT CCCTGTTCGG GCGC                                            24

(2) INFORMATION FOR SEQ ID NO:3:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

TACTAGGAGA CCAGCTTGAG CCTG                                            24

(2) INFORMATION FOR SEQ ID NO:4:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

TGCTGGAGTT TCTCTCGCCT GGGT                                            24
```

METHOD FOR PRODUCING A VIRUS FROM AN AFRICAN GREEN MONKEY KIDNEY CELL LINE

This application is a divisional of application Ser. No. 08/790,598, filed Jan. 29, 1997, which is a division of application Ser. No. 08/351,079, filed on Nov. 30, 1994, now U.S. Pat. No. 5,646,033. The disclosure of these applications is incorporated by reference in its entirety herein.

STATEMENT AS TO RIGHTS TO THE INVENTION MADE UNDER FEDERALLY SPONSORED RESEARCH AND DEVELOPMENT

Part of the work performed during development of this invention utilized U.S. Government funds. The U.S. Government has certain rights in this invention (National Institute of Allergy and Infections Diseases Contract No. N01-AO-35154).

FIELD OF INVENTION

The invention relates to a novel African Green Monkey Kidney (AGMK) cell subtrate that supports the efficient replication of human and animal rotaviruses, astroviruses, enteroviruses including the Sabin live attenuated poliovirus vaccine strains, hepatitis A virus and respiratory viruses such as respiratory syncytial virus, parainfluenza viruses, and influenza A and B viruses.

The invention is also useful for the production of virus suspensions suitable for use in vaccines for immunization of humans.

BACKGROUND OF INVENTION

Rotaviruses are major causal agents of acute gastroenteritis in man with a worldwide distribution. Enteroviruses have been implicated in infections of the gastrointestinal tract, the respiratory system and in aseptic meningitis. Respiratory syncytial virus (RSV), the parainfluenza viruses and the influenza viruses have been shown to be the major causal agents of serious pediatric diseases such as croup, bronchiolitis and pneumonia, while the influenza viruses are the major cause of serious febrile respiratory tract illness in adults. Hepatitis A virus is the cause of hepatitis A, one of the major infectious diseases of the liver.

Rotavirus infections occur world-wide and are responsible for a large proportion of severe, life-threatening, often fatal diarrheal disease. Most rotavirus disease is caused by the four major human rotavirus serotypes but other serotypes are being discovered continuously. The latter are usually restricted in geographic distribution, but they could become a larger problem at any time. World-wide, the human rotaviruses are the major etiologic agents of serious acute gastroenteritis in infants and young children and on occasion can cause debilitating diarrhea in adults. It has been estimated by the World Health Organization that rotaviruses are responsible for one million fatal diarrheal illnesses each year in infants and young children in developing countries.

The most important cause of serious viral respiratory illness in children is respiratory syncytial virus (RSV). The parainfluenza viruses, influenza viruses, and adenoviruses are also important in this regard. Especially in the case of respiratory syncytial virus (RSV), of which there are two major subgroups A and B, immunity does not appear to be long-lasting and re-infections can and do occur with high frequency during infancy, through the pre-school period, and throughout adult life. The parainfluenza viruses, of which there are four major types—1, 2, 3 and 4—have been implicated as important causes of croup, bronchiolitis and pneumonia in infants and young children. These viruses are second only to RSV as a cause of severe viral respiratory tract disease. In adults, the influenza viruses are a major cause of mortality in older persons with underlying acute or chronic cardiac or pulmonary disease. The serious systemic disease manifestations of influenza virus infections are well known and the frequent antigenic shifts in serotype [A/JH1N1, A/H3N2 and B] necessitate changes in the composition of the strains included in the yearly vaccine preparations.

The enteroviruses, which are a subgroup of picornaviruses consisting of polioviruses, Coxsackie viruses and echoviruses, have been shown to cause a broad spectrum of illnesses. These illnesses include paralytic disease, encephalitis, aseptic meningitis, pleurodynia, exanthems, and pericarditis with some of the infections resulting in debilitating sequelae. Hepatitis A virus, also a picornavirus, is a major cause of sporadic as well as epidemic hepatitis.

According to convention, semi-continuous cell systems which are diploid and have a finite longevity in terms of the number of passages that can be achieved in the laboratory are designated as cell strains, whereas continuous cell systems that are aneuploid and can be passaged indefinitely in the laboratory (i.e., are imnortal) are designated as cell lines. A limiting factor in the development of vaccines for combating the maladies caused by a number of these infectious agents has been the lack of availability of an acceptable cell strain or line capable of supporting the growth of these viruses to a concentration suitable for use in vaccine production. Convenient and susceptible cell strains and/or lines that can be cultured using relatively high split ratios (i.e., the preparation of multiple tissue culture vessels from a single culture) and which can be approved for human use by the Center for Biologics Evaluation and Research (CBER) of the Food and Drug Administration (FDA) are needed to enable and facilitate vaccine development for certain medically important viruses that are uncontrolled currently.

Semi-continuous or continuous cell culture systems capable of supporting the growth of hybrid rotaviruses, hereafter designated human x animal rotavirus reassortants, have included the simian cell strain, FRhL-2, and the simian cell lines, CV-1 and Vero. Live virus vaccines produced in these cells have received CBER, FDA approval for Phase I and II studies. Henceforth, we will refer to these cell strains or lines as certified cell strains or lines to distinguish them from cell strains or lines that have been licensed for production of human vaccines. To date, only two semicontinuous cell culture systems, WI-38 and MRC-5, both human fetal diploid cell strains, have been licensed for use in virus vaccines. These cell strains will be referred to as licensed cell strains. Currently, there are no licensed continuous cell lines.

The above mentioned certified cell strain or lines (FRhL-2, CV-1 and Vero) are limited in their ability to support the growth of completely homologous human rotaviruses, i.e., rotaviruses that derive each of their 11 RNA gene segments from a human rotavirus. In addition, the FRhL-2 cell strain, with a maximum 1:3 split ratio capability, is limited in its ability to support the growth of important RSV. The CV-1 cells, with a maximum 1:4 split ratio capability, have not supported the growth of many viral agents to a level satisfactory for vaccine production. The Vero cells, with a split ratio of 1:6–1:10, are limited in their ability to support the growth of a number of enteroviruses and fail to support the efficient growth of completely homologous human rotaviruses.

Naturally occurring strains of hepatitis A virus (HAV), a picornavirus distantly related to the enteroviruses, do not grow well in any cell type during primary isolation and must be adapted to growth in cells of primate origin before the level of virus replication required for vaccine development and production can be achieved. Inactivated whole-virus HAV vaccines grown in fetal human fibroblast MRC-5 cells have been developed, but the low split ratio of 1:2 required by these cells, the low viral titers achieved, and the prolonged cultivation time of up to two weeks necessary for maximum yield of viral antigen make such vaccines expensive. Growth of HAV in simian CV-1, FRhK-4 (a fetal rhesus monkey kidney cell line), FRhK-6 (another fetal rhesus monkey kidney cell line) and Vero cells has been variable depending on the strain and passage level of virus, but generally is suboptimal. Best growth has been obtained in a cloned cell line, designated clone 11-1, derived from FRhK-4 cells, but these cells contain bovine papilloma virus sequences and thus, are not suitable for vaccine development.

Candidate live attenuated and inactivated HAV vaccines have been developed by adaptation of the virus to growth in primary African green monkey (AGMK) cells but such vaccines are not economically feasible because of the extreme difficulty of obtaining sufficient primary AGMK cells that are free of extraneous viral agents of monkey origin. Live attenuated and inactivated HAV vaccine candidates have been adapted to growth in MRC-5 cells, a human fetal diploid cell strain, but such adaptation has consistently led, respectively, to over-attenuation of the live attenuated virus for humans and a relatively sparse yield of inactivated virus vaccine.

Thus, there remains a need for a cell strain or line capable of supporting the efficient growth of a large number of human viral pathogens such as the human rotaviruses, enteroviruses, HAV, and respiratory viruses of major medical importance including RSV, influenza viruses and parainfluenza viruses. Such a cell strain or line would facilitate the development and production of commercially useful and effective vaccines. There is a pressing need for the development of vaccines against these viruses in order to prevent severe viral diseases of infants, children, adults and the elderly.

Therefore, the availability of a single cell strain or line capable of supporting the efficient replication of those viral agents responsible for a significant number of childhood and adult diseases would provide a significant advancement in the formulation and production of multivalent vaccines.

SUMMARY OF THE INVENTION

The present invention is directed to a cell substrate that substantially overcomes the limitations of previously established cell strains or lines. The serially passaged cells of the present invention are derived from the paired kidneys of an African green monkey and support the efficient growth of medically important human rotaviruses, astroviruses, picornaviruses such as enteroviruses including the Sabin live attenuated poliovirus vaccine strains and hepatitis A virus, and respiratory viruses such as respiratory syncytial virus, parainfluenza viruses, and influenza A and B viruses.

The AGMK cells of the invention are designated as a cell substrate because it is not clear at this time whether they constitute a cell strain or cell line. It is probable that they are a cell line because they are aneuploid, an essential and defining property of cell lines. However, the AGMK cells have been passaged serially only 30 times and assignment of cell immortality, one of the other defining features of a cell line, requires more than 50 serial passages.

At the 30th passage there was no diminution of viability, or ability to grow nor was there any other outward sign of senescence. Furthermore, the AGMK cells have been split 1:4 or 1:8 at each of these passages, a split ratio that is characteristic of cell lines but not cell strains which usually can not be split more than 1:2.

An important advantage of the present invention is that the cell substrate, based on currently promulgated guidelines (i.e., "Points to Consider in the Characterization of Cell Lines Used to Produce Biologicals" (May 1993)) and state-of-the-art testing, has been demonstrated to be free of detectable adventitious microbial agents. This feature allows the cell substrate to be employed for the growth of viruses, such as the human rotaviruses and hepatitis A virus, which have a very highly restricted and narrow tissue culture host range. The unavailability of such a clean cell system prior to this invention has hampered vaccine development for these viruses. In addition, the cell substrate can be used in studies which require cultures of monkey kidney cells free of simian adventitious agents. The commercially available monkey kidney cell cultures are frequently contaminated with these agents, which negate or becloud any results obtained and preclude their use in vaccines destined for administration to humans. This invention also offers the advantage of a cell substrate which can be trypsinized and split in ratios ranging from 1:4 to 1:8 depending upon vessel size and time constraints imposed by vaccine production deadlines.

Additional features and advantages of the invention will be set forth in the description which follows or may be learned by practice of the invention. The objectives and other advantages of the invention to be realized and attained will be cited in the written description and claims hereof as well as the appended drawings.

To achieve these and other advantages and in accordance with the purpose of the invention, as embodied and broadly described, the invention provides a cell line derived from the paired kidneys of an African green monkey, which is free of demonstrable adventitious microbial agents. The invention also provides a method for establishing the cell line by the enzymatic disaggregation of the paired kidneys from an African green monkey and continuous cultivation of the resulting cells. In addition, the invention provides a method for recovering and serially propagating specific viruses in the cell line that subsequently can be used for production of a viral vaccine.

BRIEF DESCRIPTION OF THE FIGURES

FIG. 2 outlines the passage history from single ampoule from the MWCB to post-production history.

DETAILED DESCRIPTION OF THE INVENTION

Figure 1:
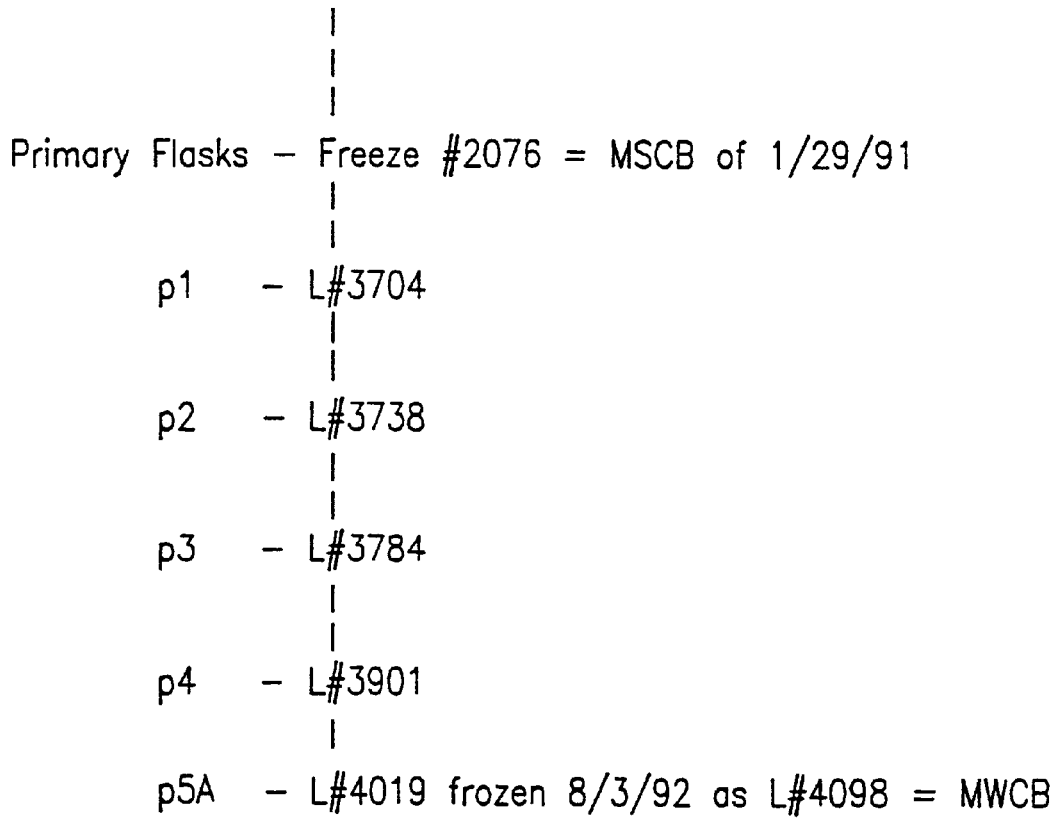
FIG. 1 outlines the passage history from a single ampoule of a disassociated African Green Monkey Kidney sample to the preparation of a Master Seed Cell Bank (MSCB) and a Master Working Cell Bank (MWCB).

The present invention provides a cell line derived from a pair of African green monkey kidneys. The cell line is free of demonstrable viable adventitious microbial agents. In addition, the cell line is capable of supporting the growth of viruses such as human rotaviruses, astroviruses, enteroviruses, respiratory viruses and hepatitis A and is, therefore, useful for propagating viruses necessary for the production and formulation of a number of effective vaccines on a scale that makes such vaccines commercially feasible.

Specifically, the present invention relates to an aneuploid cell substrate with chromosome counts in the diploid range which was initiated by the enzymatic disaggregation of paired kidneys from a female Cercopithecus African green monkey. A deposit of the cell line at passage No. 13, Lot 6500 has been made with the American Type Culture Collection, 10801 University Boulevard, Manasses, Va. 20110-2209 USA, on Nov. 4th 1994 and has been assigned accession No. ATCC# CRL 11756.

This cell line was deposited according to the Budapest Treaty. If the deposited culture should die or otherwise become lost or destroyed, this cell line will be replaced with a living culture containing this cell line. This cell line will be maintained for a period of at least 30 years after the date of deposit, and for a period of at least 5 years after the most recent request for a sample. This cell line will be made available if a Patent Office signatory to the Budapest Treaty certifies one's right to receive, or if a U.S. Patent is issued to this application or any other applications claiming benefit of priority to this application.

The present invention also provides a method of establishing a cell substrate capable of at least 30 serial passages that is initially derived by the enzymatic disaggregation of kidneys from an African green monkey. In addition, the invention provides a method for recovery and growth of specific viruses, a necessary first step for subsequent vaccine production.

It will be apparent to those skilled in the art that various modifications and variations can be made in the cell substrate of the present invention and in its uses without departing from the spirit or scope of the invention. Thus, it is intended that the present invention covers the modifications and variations of this invention provided they come within the scope of the appended claims and their equivalents.

Having now described the invention in general terms, it will be better understood by reference to certain examples which are included herein for the purpose of illustration only and are not intended to be limiting unless otherwise specified.

EXAMPLE 1

Derivation of the AGMK Cell Substrate

Source: The cell substrate was derived from the kidneys of an African green monkey from a colony that had been established on Barbados. The cells are free of any demonstrable viable adventitious microbial agents. The microbial agents include, but are not limited to bacteria, fingi, mycobacteria, mycoplasma and simian agents such as retroviruses, foamy viruses, hemadsorbing viruses, herpes-like viruses and multinucleating or syncytial viruses. The kidneys were processed using conventional enzymatic disaggregation technology. The resulting kidney cell suspension was used to initiate 3 primary flask [T150 cm$^2$] cultures with the remainder, designated as Freeze #2129, distributed into multiple ampules and frozen for storage in a liquid nitrogen freezer. The primary flask cultures labelled A, B and C, were processed as follows:

Flask A: On day 14 split 1:2=1-A-1 & 1-A-2 with one of these flasks split on day 28 1:2=2-A-1 & 2-A-2

Flask B: On day 21 split 1:2=1-B-1 & 1-B-2 with one of these flasks split on day 35 1:2=2-B-1 & 2-B-2

Flask C: Not split

The maintenance medium consisted of Eagle's Minimal Essential Medium (EMEM)+5% fetal bovine serum (heat inactivated at 56° C. for 30 min.)+1% glutamine (200 mM). All flask cultures were refed with 100 ml of fresh maintenance medium on a weekly basis for a total incubation period of 9 weeks based on the initial planting date. The cultures were negative for hemadsorption and CPE (cytopathic effect), the latter determined by microscopic examination after fixation and staining.

The passage history from a single ampule to the preparation of the Master Seed Cell Bank (MSCB) and the Master Working Cell Bank (MWCB) is depicted in FIG. 1. Cultures were handled in a Class 100 Laminar Flow Hood and in an area where only normal tissue cultures and/or vaccine-designated cell systems were cultured. Cultures were serially passaged employing a 1:4 to 1:6 split ratio with incubation at 36° C. ±1° C. and utilizing the following methodology:

1. Cell films were washed with Hanks' Balanced Salt Solution (HBSS) without Ca$^{++}$and Mg$^{++}$.
2. Films were disaggregated by the addition of a trypsin-EDTA solution and incubation at 36° C. ±1° C. for 4–5 minutes.
3. Films were broken up by rapid pipetting with the cells suspended in the growth medium [EMEM+10% fetal bovine serum +1% glutamine] and seeded into appropriate size culture vessels.

The passage history from single ampules from the MWCB to the post-production testing is outlined in FIG. 2.

EXAMPLE 2

Testing of the Master Working Cell Bank - Passage 7A. Lot#4214

1. KARYOTYPING AND SPECIES IDENTIFICATION:

Passage 7A, Lot #4214 was characterized by Giemsa banded chromosome analysis and reaction with species-specific antisera and isoenzyme analysis.

a. Cytogenic Characterization: Conventional chromosome staining (non-banded) was utilized to determine chromosome count ploidy distribution per 100 metaphases. Identifiable markers and aberrations were analyzed for 50 metaphases.

Chromosome banding by trypsin-Giemsa was utilized to analyze the karyotype and identify specific chromosome markers. Species confirmation was made using G-banding patterns and chromosome morphology. The procedures used were modifications of those described by Peterson, W. D., Jr., Simpson, W. F., and Hukku, B., Cell culture characteristics: Monitoring for cell identification, in Jakoby, W. B. and Pastan, I. H., eds., *Methods in Enzymology* 58: 164–178, 1979; and Seabright, M., A rapid banding technique for human chromosomes, *Lancet*, ii: 971–972, 1971.

The cell line was identified as an aneuploid female Cercopithecus (African green) monkey (XX) with chromosome counts in the diploid range. Most of the chromosomes were normal and present in two copies each. Normal chromosome D was monosomic and a single marker D chromosome was observed.

b. Species Identification of Cell Culture: The ability of the test cell preparation to react with species-specific antisera was determined using the fluorescent antibody technique as described by Peterson et al., supra. The cells reacted with monkey antiserum but not with mouse or hamster antiserum.

C. Isoenzyme Analysis: Enzyme preparations were made from the test article cells. The electrophoretic migration distances of the enzymes were compared with known migration distances of enzymes in various mammalian species as described by Halton, D. M., Peterson, W. D., Jr., and Hukku, B. Cell culture quality control by rapid isoenzymatic characterization, *In Vitro* 19: 16–24, 1983; Ottenbreit, M. J., Halton, D. M., and Peterson, W. D., Jr., Rapid isoenzyme analysis of cell cultures by agarose electrophoresis, I. Interspecies identification, *J Tissue Culture Methods*, 6: 107–110, 1982; and II. Intraspecies identification of human cell lines, *J. Tissue Culture Methods*, 8: 125–130, 1986.

The electrophoretic mobilities of enzymes glucose-6-phosphate dehydrogenase (G6PD), nucleoside phosphorylase (NP), malate dehydrogenase (MDH) and lactate dehydrogenase (LDH) present in an extract prepared from the test cells were comparable to those of a Cercopithecus (African green) monkey control cell preparation. No extra bands were observed on the electrophoresis films that might suggest the presence of cells of a species other than that of the cell culture.

Cells other than those of the submitted culture (MWCB, Passage 7A, Lot#4214) were not detected in the culture by either isoenzyme analysis or by cytogenic evaluation.

2. DETECTION OF RETROVIRUSES a. Detection of Retrovirus Particles by Electron Microscopic Examination: A cell pellet of the test article cells (MWCB, Passage 7A, Lot#4214) was prepared and examined for the presence of virus particles by transmission electron microscopy. No retrovirus-like particles were found in the 200 cells observed.

b. Detection of Retrovirus Reverse Transcriptase in the Presence of DNA-Dependent DNA Polymerase: The test article (MWCB, Passage 7A, Lot#4214) was analyzed for the presence of types B, C and D retrovirus reverse transcriptase and cellular DNA polymerase activity. No evidence for the presence of retrovirus reverse transcriptase was observed.

The results are presented in Table I—A, B and C.

TABLE I-A

Reverse Transcriptase and DNA Polymerase Activities in Test Article AGMK MWCB Cell Cultures: p7A, L-4214

| Sample | Adjusted Reverse Transcriptase[a] (rAdT) $Mn^{++}$ | Reverse Transcriptase[b] (rAdT) | | DNA Polymerase[b] (dAdT) | |
|---|---|---|---|---|---|
| | | $Mn^{++}$ | $Mn^{++}$ | $Mn^{++}$ | $Mn^{++}$ |
| Test Article | | | | | |
| Undiluted | 22 | 25 | 0 | 7 | 0 |
| Diluted 2-fold in medium[c] | 6 | 8 | 0 | 19 | 1 |
| Diluted 2-fold in R-MuLV[d] | | 20,837 | 433 | 10 | 0 |
| Diluted 2-fold in DNA polymerase[e] | | 795 | 6 | 7,137 | 508 |
| Positive and Negative Controls[f] | | | | | |
| R-MuLV diluted 2-fold in medium[g] | | 18,589 | 549 | 12 | 0 |
| DNA Polymerase diluted 2-fold in medium[g] | | 1,079 | 25 | 5,443 | 542 |
| SMRV[h] | | 2,585 | 48,289 | 211 | 396 |
| Stabilization Buffer[i] | | (63) | (59) | (67) | (58) |
| Medium[c] | | (65) | (57) | (65) | (52) |
| Medium[g] | | (78) | (56) | (62) | (49) |

[a]Reverse transcriptase activity adjusted for the effect of DNA polyrnerase (Table 2 and Methods).
[b]Expressed as counts per minute $^3$H-thymidine triphosphate incorporated (mean duplicates minus background).
[c]EMEM + 10% serum subtracted from test article samples.
[d]R-MuLV (Rauscher Murine Leukemia Virus) - Type C virus positive control.
[e]DNA polymerase - Positive control; prepared from mink lung cells.
[f]Control monitoring background of incorporation of $^3$H-thymidine triphosphate (reaction mixture with undiluted test article minus template primers) = 61 cpm (medium background not subtracted).
[g]EMEM + 10% serum subtracted from R-MeLV and DNA polymerase positive controls.
[h]SMRV (Squirrel Monkey Retrovirus Preparation) - Type D virus positive control.
[i]Stabilization buffer used to dilute SMRV positive control.

TABLE I-B

Adjustment of Reverse Transcriptase Values for Interference by Polymerase in Test Article AGMK MWCB Cell Cultures: p7A, L-4214

| | RT Assay (CPM) | | DNA Polymerase Assay (CPM) | |
|---|---|---|---|---|
| | Observed[a] ($Mn^{++}$) | Adjusted[b] ($Mn^{++}$) | Observed ($Mn^{++}$) | DNA Polymerase × Slope |
| Test Article | | | | |
| Undiluted | 25 | 22 | 37 | 3 |
| Diluted 2-fold in medium[c] | 8 | 6 | 19 | 2 |

[a]Unadjusted $^3$H-TTP incorporation catalyzed by RT. May include effects by cellular DNA polymerase.
[b]Adjusted $^3$H-TTP incorporation catalyzed by RT = Observed RT - (DNA polymerase × Slope). Slope = 0.08.
[c]Medium used to dilute test article.

TABLE I-C

Reverse Transcriptase and DNA Polymerase Activities
in a DNA Polymerase Preparation from Reverse
Transcriptase-Negative Cell Cultures
(Used for Determining Interference in Reverse
Transcriptase Assay by DNA Polymerase)

| DNA Polymerase[a] | Reverse Transcriptase[b] (rAdT) | | DNA Polymerase[b] (dAdT) | |
|---|---|---|---|---|
| | $Mn^{++}$ | $Mg^{++}$ | $Mn^{++}$ | $Mg^{++}$ |
| Sample 1 | 116 | 10 | 1,898 | 198 |
| Sample 2 | 187 | 0 | 2,634 | 0 |
| Sample 3 | 547 | 6 | 6,690 | 119 |
| Sample 4 | 574 | 3 | 8,529 | 81 |
| Sample 5 | 1,196 | 27 | 14,315 | 1,222 |

[a]DNA polymerase prepared from mink lung cells.
[b]Expressed as counts per minute $^3$H-thymidine triphosphate incorporated [mean duplicates minus background (medium)].

EXAMPLE 3

Post-Production Cell Testing

1. Karyotyping and Species Identification

The AGMK cells at Passage 17A, Lot #4706 were characterized by Giemsa banded chromosome analysis and reaction with species-specific antisera and isoenzyme analysis.

The cells were identified as aneuploid female Cercopithecus (African green) monkey (XX, XXX) with chromosome counts in the hypodiploid to hyperdiploid range. All karyotypes examined contained a single normal Cercopithecus monkey marker chromosome (Group D) and a second partially deleted Cercopithecus monkey D group marker chromosome.

The electrophoretic mobilities of the enzymes G6PD, NP, MDH and LDH present in an extract prepared from the test cells were comparable to those of Cercopithecus (African green) monkey control cell preparation. No extra bands were observed on the electrophoresis films that might suggest the presence of cells of a different species in the cell culture. The cells reacted with monkey antiserum but not with mouse antiserum.

Cells other than those of the submitted culture (Passage 17A, Lot #4706) were not detected in the culture by either antisera reaction, isoenzyme analysis or by cytogenic evaluation. The chromosome pattern was similar to that previously observed for cells in the MWCB, Passage 7A, Lot #4214 and specifically related these cells (Passage 17A, Lot #4706) to the former.

2. Detection of Retroviruses a. The test article, AGMK Passage 17A, Lot #4706, was analyzed for the presence of types B, C and D retrovirus reverse transcriptase and cellular DNA polymerase activity. The cells were grown in the presence of 30 μg/ml bromodeoxyuridine for 24 hours (day 0 to day 1) and then refed with medium without inducer. Culture fluids (unconcentrated and concentrated 20-fold) were harvested on days 2, 3 and 4. No evidence for the presence of retrovirus reverse transcriptase activity was observed in the test article. The results are presented in Table II—A, B and C.

b. Detection of Retrovirus Particles by Electron Microscopic Examination: Cell pellets were prepared from the treated and untreated cultures harvested on day 4 and examined for the presence of virus particles by transmission electron microscopy. No retrovirus-like particles were found in the 200 cells observed.

c. Detection of Simian T-Lymphotropic Virus (STLV) in Test Article (AGMK, Passage 17A, Lot #4743) by Polymerase Chain Reaction (PCR) Technique: The polymerase chain reaction (PCR) provides a method for detection of extremely low numbers of viral nucleic acid sequences, which would not be detectable without amplification. When coupled with a pre-PCR reverse transcriptase step, RNA sequences may be amplified, thus allowing detection of free virus. The protocol used allowed for the amplification of either DNA or RNA derived STLV-specific sequences. The PCR products were tested by Southern blotting, using chemiluminescent enzyme-linked probe hybridization to the blot.

When tested with the STLV pot primers SK 110/SK111, STLV-specific product was not detected in test article reactions, each of which represented 1.0 μg nucleic acid extracted from the test article. In the positive control series, which contained the equivalent of 0.001 μg, 0.01 μg, 0.1 μg or 1 μg of nucleic acid extracted from a cell line infected by STLV ($STLV_{mn103}$), STLV-specific product was detected in all reactions. On the basis of failure to detect reactivity with STLV primers, the test article was judged to be negative for STLV nucleic acid sequences.

d. Detection of the Simian Immunodeficiency Virus in Test Article (AGMK, Passage 18A, Lot #5506): Total cellular DNA was extracted from the test article and subsequently tested for the presence of $SIV_{agm}$ virus sequences using primers that amplify a 200 bp fragment of the LTR. This involved PCR with nested sets of primers as follows:

```
Outer set #1807 F: CCTCAGAGCTGCATAAAAGCAGAT (SEQ ID NO:1)
          #1808 R: TCACTCAAGTCCCTGTTCGGGCGC (SEQ ID NO:2)
Inner set #1809 F: TACTAGGAGACCAGCTTGAGCCTG (SEQ ID NO:3)
          #1810 R: TGCTGGAGTTTCTCTCGCCTGGGT (SEQ ID NO:4)
```

These primers were designed for the conserved U5 and R regions of the LTR and are capable of amplifying all subtypes of $SIV_{agm}$. The predicted 200 bp fragment was amplified from DNA extracted from a chronically-$SIV_{agm}$ infected cell line ($SIV_{agm}155CEM_{ss}$) but the African green monkey cells did not have detectable $SIV_{agm}$ sequences by Southern blot analysis.

3. Tumorigenicity in Athymic Nude Mice

The cells were found to be non-tumorigenic after being clinically evaluated for 150 days. Athymic nude mice were inoculated subcutaneously with approximately $1 \times 10^7$ test article cells (AGMK Passage 17A, Lot #4889). Athymic nude mice were similarly inoculated with positive control cells. All 10 positive control inoculated mice had tumors at the site of inoculation. No metastases were observed in the inoculation site (skin), lung, lymph nodes, liver, kidney, spleen or brain of mice inoculated with the test article.

TABLE II-A

Reverse Transcriptase and DNA Polymerase Activities
in Unconcentrated AGMK Passage 17A, Lot #4706

| Sample | Reverse Transcriptase[b] (rAdT) | | DNA Polymerase[b] (dAdT) | |
|---|---|---|---|---|
| | $Mn^{++}$ | $Mg^{++}$ | $Mn^{++}$ | $Mg^{++}$ |
| Test Article Cells[b] | | | | |
| DAY | | | | |
| 2  Untreated | 0 | 0 | 227 | 0 |
| Treated | 29 | 0 | 485 | 85 |
| 3  Untreated | 0 | 0 | 265 | 6 |
| Treated | 0 | 0 | 243 | 0 |
| 4  Untreated | 35 | 0 | 711 | 29 |
| Treated | 48 | 0 | 723 | 26 |

[a]Expressed as counts per minute $^3$H-thymidine triphosphate incorporated (mean duplicates minus background).
[b]Culture fluids from test article cells.

TABLE II-B

Reverse Transcriptase and DNA Polymerase Activities
in AGMK Passage 17A, Lot #4706
Concentrated 20-fold

| Sample | Reverse Transcriptase[b] (rAdT) | | DNA Polymerase[b] (dAdT) | |
|---|---|---|---|---|
| | $Mn^{++}$ | $Mg^{++}$ | $Mn^{++}$ | $Mg^{++}$ |
| Test Article Cells[b] | | | | |
| DAY | | | | |
| 2  Untreated | 9 | 0 | 18 | 87 |
| Treated | 0 | 0 | 15 | 104 |
| 3  Untreated | 6 | 0 | 32 | 125 |
| Treated | 9 | 3 | 19 | 136 |
| 4  Untreated | 22 | 3 | 14 | 114 |
| Treated | 122 | 2 | 2,423 | 516 |

[a]Expressed as counts per minute $^3$H-thymidine triphosphate incorporated (mean duplicates minus background).
[b]Culture fluids from test article cells.

TABLE II-C

Reverse Transcriptase and DNA Polymerase Activities
in AGMK Passage 17A, Lot #4706

| Sample | Reverse Transcriptase[a] (rAdT) | | DNA Polymerase[b] (dAdT) | |
|---|---|---|---|---|
| | $Mn^{++}$ | $Mg^{++}$ | $Mn^{++}$ | $Mg^{++}$ |
| Positive and Negative Controls | | | | |
| R-MuLV[c] | 65,913 | 2,230 | 0 | 16 |
| SMRV[d] | 12,031 | 133,798 | 1,274 | 2,825 |
| DNA Polymerase[e] | 7,015 | 57 | 60,197 | 6,646 |
| Medium[f] | (163) | (74) | (242) | (107) |

TABLE II-C-continued

Reverse Transcriptase and DNA Polymerase Activities
in AGMK Passage 17A, Lot #4706

| Sample | Reverse Transcriptase[a] (rAdT) | | DNA Polymerase[b] (dAdT) | |
|---|---|---|---|---|
| | $Mn^{++}$ | $Mg^{++}$ | $Mn^{++}$ | $Mg^{++}$ |
| Stabilization Buffer[g] | (53) | (59) | (46) | (44) |
| Medium[h] | (146) | (136) | (321) | (148) |

[a]Expressed as counts per minute $^3$H-thymidine triphosphate incorporated (mean duplicates minus background).
[b]Culture fluids from test article cells.
[c]R-MuLV (Rauscher murine leukemia virus) - Type C virus positive control.
[d]SMRV (Squirrel Monkey Retrovirus Preparation) - Type D virus positive control.
[e]DNA polymerase - Positive control; prepared from mink lung cells.
[f]Medium - Subtracted from unconcentrated, untreated and treated samples.
[g]Stabilization buffer - Negative control; subtracted from positive controls and concentrated samples.
[h]Medium - Subtracted from R-MulV and DNA polymerase positive controls.

EXAMPLE 4

Post-Production Testing for Microbial Sterility

1. Bacterial Sterility in Fluid Thioglycollate Medium

Each of 10 culture tubes (9–10 ml medium per tube) was inoculated with 1.0 ml of the AGMK cell suspension (Passage 17A, Lot #4706) containing approx. $5 \times 10^5$ cells per ml. Each of 5 tubes was inoculated with 1.0 ml of the original growth medium. Ten cultures were included as uninoculated controls. All cultures were vortex mixed and incubated at 32° C. ±2° C. for 21 days with observations made on days 1, 3, 6, 8, 10, 13, 15, 17, 20 and 21. No growth was observed in any of the 25 cultures.

2. Fungal Sterility in Soybean Casein Digest Medium

Each of 10 culture tubes (9–10 ml medium per tube) was inoculated with 1.0 ml of the AGMK cell suspension (Passage 17A, Lot #4706) containing approx. $5 \times 10^5$ cells per ml. Each of 5 tubes was inoculated with 1.0 ml of the original growth medium. Ten cultures were included as uninoculated controls. All cultures were vortex mixed and incubated at 22° C.±2° C. for 21 days with observations made on days 1, 3, 6, 8, 10, 13, 15, 17, 20 and 21. No growth was observed in any of the 25 cultures.

3. Mycobacterial Sterility in Lowenstein-Jensen Egg Medium

Each of 10 slant culture tubes was inoculated with 0.5 ml of the AGMK cell suspension (Passage 17A, Lot #4706) containing approx. $5 \times 10^5$ cells per ml. Each of 10 culture slants was inoculated with 0.5 ml of the original growth medium. Six cultures were included as uninoculated controls. All cultures were incubated at 36° C.±1° C. horizontally for the first 24 hours and vertically for the remainder of the 8 week observation period with weekly observations for growth. On day 28, one cell suspension inoculated culture was found contaminated with a mold. No growth was observed in any of the remaining 25 cultures after 8 weeks. This assay was repeated with AGMK Passage 18A, Lot #4918, but using 6 culture slants inoculated with the original growth medium. No growth was observed in any of the 22 cultures after 8 weeks. The results of the above Microbial Sterility Assays are summarized in Table III.

4. Mycoplasma Sterility

The assay for mycoplasma was performed using both the direct Broth Enrichment and Agar Procedures and the indirect Indicator Cell Culture Procedure with the AGMK cell suspension (Passage 17A, Lot #4706) containing approximately $5 \times 10^5$ cells per ml. The cell suspension was found to be negative for mycoplasmas by all procedures.

TABLE III

Microbial Sterility Test Results on the AGMK Cell Suspension -
Passage 17A, Lot #4706 and #4918 at Approximately $5 \times 10^5$ Cells/ml

| Culture Medium | No. | Vol. Per Culture (ml) | Temp. | On Test | Off Test | Results |
|---|---|---|---|---|---|---|
| Fluid Thioglycollate | | | | | | |
| (FIM) LOT VVPL #122-50 | 10 | — | 32° C. | 1/05/93 | 1/26/93 | No Growth |
| Cell Suspension #4706 | 10 | 1.0 | (±2° C.) | | | | | No Growth |
| Culture Medium | 5 | 1.0 | | 1/05/93 | 1/26/93 | No Growth |
| Soybean-Casein-Digest | | | | | | |
| (SCDM) LOT VVPL #112-51 | 10 | — | 22° C. | 1/05/93 | 1/26/93 | No Growth |
| Cell Suspension #4706 | 10 | 1.0 | (±2° C.) | | | | | No Growth |
| Culture Medium | 5 | 1.0 | | 1/05/93 | 1/26/93 | No Growth |
| Lowenstein-Jensen Egg | | | | | | |
| Medium - LOT #C3CPPB | 6 | — | 36° C. | 1/05/93 | 3/02/93 | No Growth |
| Cell Suspension #4706 | 10 | 0.5 | (±1° C.) | | | | | 1/10 mold |
| Culture Medium | 10 | 0.5 | | | | on day 28 |
| | | | | 1/05/93 | 3/02/93 | No Growth |
| Lowenstein-Jensen Egg | | | | | | |
| Medium - LOT #H3CTGX | 6 | — | 36° C. | 2/23/93 | 4/20/93 | No Growth |
| Cell Suspension #4918 | 10 | 0.5 | (±1° C.) | | | | | No Growth |
| Culture Medium | 6 | 0.5 | | 2/23/93 | 4/20/93 | No Growth |

EXAMPLE 5

In Vitro Tissue Culture Purity and Safety Tests for the Detection of Viable Adventitious Microbial Agents These assays were performed in roller tube cultures of the following tissue culture systems: Serially passaged African green monkey kidney (AGMK); Primary Human Amnion (PHA); Vero; Primary Rabbit Kidney (PRK); Whole Human Embryo Fibroblast (Fl 5000); and Human Carcinoma of the Larynx (H.Ep-2). Cultures were maintained on Medium EMEM containing 2–10% fetal bovine serum (gamma irradiated) plus antibiotics: gentamicin, 100 µg/ml; neomycin, 50 µg/ml; and fungizone, 2.5 µg/ml. Cultures were refed with 2 ml of maintenance medium prior to inoculation.

Testing Procedures: The cell suspensions (Lots #4742/3, #4755 or #4889 containing approximately $5 \times 10^5$ cells per ml) were inoculated in 0.5 ml amount per each of 28 roller tubes per tissue culture system. Cultures were incubated at 36° C.±1° C. for 14 days with periodic microscopic examination for any cytopathic effect (CPE) and/or cellular degeneration. When necessary to maintain the integrity of the cell films, cultures were refed with 2 ml of fresh maintenance medium. Additional groups of 28 roller tubes per tissue culture system were included as uninoculated controls.

On the 7th–8th day of incubation, 6–9 tubes from each series (inoculated and controls) were removed and tested for hemadsorption with 3 red blood cell (RBC) suspensions (guinea pig at 0.1%, chicken at 0.075%, or human at 0.1% in PBS, pH 7.2). Films were rinsed once in the phosphate-buffered saline (PBS) prior to the addition of 1 ml of the RBC suspension employing 2–3 tubes per RBC. Initially, tubes were incubated at 2°–8° C. for a minimum of 30 minutes and examined microscopically for any signs of hemadsorption. Following manual shaking, tubes were incubated at 35°–37° C. for a minimum of 30 minutes and re-examined microscopically for hemadsorption. All cultures were inactive for hemadsorption with all 3 suspensions and at both temperatures. On day 14, after final microscopic examination, the cultures were divided, depending on the specific tissue culture system for final testing. AGMK, PHA and F15000 Tube Cultures were divided as follows:

1. 9 tubes from each series were tested for hemadsorption with the 3RBC suspensions as described above for day 7–8;
2. 4 tubes from each series were fixed and stained with a solution of 5% glutaraldehyde +0.025% crystal violet and, after drying, examined microscopically for any signs of CPE;
3. 8 tubes from each series were challenged with Coxsackie A-9 virus (0.1 ml for each of 2 tubes using a $10^{-2}$, $10^{-3}$, $10^{-4}$ or $10^{-5}$ dilution) for the detection of non-CPE producing agents and/or latent agents via the interference phenomenon; and
4. One (1) tube of each series was included as an uninoculated control for the challenge virus.

Vero, PRK and H.Ep-2 Tube Cultures were divided as follows:

1. 12 tubes from each series were tested for hemadsorption with the 3 RBC suspensions as described above for day 7–8;
2. 7 tubes from each series were fixed and stained with a solution of 5% glutaraldehyde +0.025% crystal violet and, after drying, examined microscopically for any signs of CPE.

No challenge studies were carried out with the Coxsackie A-9 virus as this agent does not produce any discernible CPE in these cell systems. The results of these in vitro tissue culture purity and safety assays are summarized in Tables IV—A to F.

TABLE IV-A

Tissue Culture Purity Tests on the AGMK Cell Suspension -
Passage 17A, LOT #4742/3 at Approximately $5 \times 10^5$ Cells/ml
African Green Monkey Kidney Cells - (Passage 12, LOT #4793)

|  |  |  | Day 7 Results | | Day 14 Results | |
|---|---|---|---|---|---|---|
|  |  |  | AGMK | Controls | AGMK | Controls |
| 0.1% Guinea Pig RBC | at | 2°–8° C. | 0/2 | 0/2 | 0/3 | 0/3 |
|  | at | 35°–37° C. | 0/2 | 0/2 | 0/3 | 0/3 |
| 0.075% Chicken RBC | at | 2°–8° C. | 0/2 | 0/2 | 0/3 | 0/3 |
|  | at | 35°–37° C. | 0/2 | 0/2 | 0/3 | 0/3 |
| 0.1% Human RBC | at | 2°–8° C. | 0/2 | 0/2 | 0/3 | 0/3 |
|  | at | 35°–37° C. | 0/2 | 0/2 | 0/3 | 0/3 |
| Giemsa Stain |  |  |  |  | 0/4 | 0/4 |
| Coxsackie A-9 Virus Challenge* | at $10^{-3}$ |  |  |  | 2/2 | 2/2 |
|  | $10^{-4}$ |  |  |  | 2/2 | 2/2 |
|  | $10^{-5}$ |  |  |  | 2/2 | 2/2 |
|  | $10^{-6}$ |  |  |  | 2/2 | 2/2 |
|  | Unchallenged Controls |  |  |  | 0/1 | 0/1 |

*Coxsackie A-9 Challenge results based on a 5-day incubation at 36° C. Prior to challenge, tubes refed with 2 ml of fresh medium.

TABLE IV-B

Tissue Culture Purity Tests on the AGMK Cell Suspension -
Passage 17A, LOT #4742/3 at Approximately $5 \times 10^5$ Cells/ml
Primary Human Amnion - (PHA) - (LOT #4720)

|  |  |  | Day 7 Results | | Day 14 Results | |
|---|---|---|---|---|---|---|
|  |  |  | AGMK | Controls | AGMK | Controls |
| 0.1% Guinea Pig RBC | at | 2°–8° C. | 0/2 | 0/2 | 0/3 | 0/3 |
|  | at | 35°–37° C. | 0/2 | 0/2 | 0/3 | 0/3 |
| 0.075% Chicken RBC | at | 2°–8° C. | 0/2 | 0/2 | 013 | 0/3 |
|  | at | 35°–37° C. | 0/2 | 0/2 | 0/3 | 0/3 |
| 0.1% Human RBC | at | 2°–8° C. | 0/2 | 0/2 | 0/3 | 0/3 |
|  | at | 35°–37° C. | 0/2 | 0/2 | 0/3 | 0/3 |
| Giemsa Stain |  |  |  |  | 0/4 | 0/4 |
| Coxsackie A-9 Virus Challenge* | at $10^{-3}$ |  |  |  | 2/2 | 2/2 |
|  | $10^{-4}$ |  |  |  | 2/2 | 2/2 |
|  | $10^{-5}$ |  |  |  | 2/2 | 212 |
|  | $10^{-6}$ |  |  |  | 2/2 | 2/2 |
|  | Unchallenged Controls |  |  |  | 0/1 | 0/1 |

*Coxsackie A-9 Challenge results based on a 5-day incubation at 36° C. Prior to challenge, tubes refed with 2 ml of fresh medium.

TABLE IV-C

Tissue Culture Purity Tests on the AGMK Cell Suspension -
Passage 17A, LOT #4755 at Approximately $5 \times 10^5$ Cells/ml
Vero Cells - (Passage 143, LOT #4813)

|  |  |  | Day 7 Results | | Day 14 Results | |
|---|---|---|---|---|---|---|
|  |  |  | AGMK | Controls | AGMK | Controls |
| 00.1% Guinea Pig RBC | at | 2°–8° C. | 0/3 | 0/3 | 0/4 | 0/4 |
|  | at | 35°–37° C. | 0/3 | 0/3 | 0/4 | 0/4 |
| 0.075% Chicken RBC | at | 2°–8° C. | 0/3 | 0/3 | 0/4 | 0/4 |
|  | at | 35°–37° C. | 0/3 | 0/3 | 0/4 | 0/4 |
| 0.1% Human RBC | at | 2°–8° C. | 0/3 | 0/3 | 0/4 | 0/4 |
|  | at | 35°–37° C. | 0/3 | 0/3 | 0/4 | 0/4 |
|  | Giemsa Stain |  |  |  | 0/7 | 0/7 |

TABLE IV-D

Tissue Culture Purity Tests on the AGMK Cell Suspension -
Passage 17A, LOT #4889 at Approximately $5 \times 10^5$ Cells/ml
Rabbit Kidney Cells - (Primary, LOT #4814)

|  |  |  | Day 7 Results | | Day 14 Results* | |
|---|---|---|---|---|---|---|
|  |  |  | AGMK | Controls | AGMK | Controls |
| 00.1% Guinea Pig RBC | at | 2°–8° C. | 0/4 | 0/4 | 0/3 | 0/3 |
|  | at | 35°–37° C. | 0/4 | 0/4 | 0/3 | 0/3 |
| 0.075% Chicken RBC | at | 2°–8° C. | 0/4 | 0/4 | 0/3 | 0/3 |
|  | at | 35°–37° C. | 0/4 | 0/4 | 0/3 | 0/3 |
| 0.1% Human RBC | at | 2°–8° C. | 0/4 | 0/4 | 0/3 | 0/3 |
|  | at | 35°–37° C. | 0/4 | 0/4 | 0/3 | 0/3 |
|  | Giemsa Stain |  |  |  | 0/7 | 0/7 |

*On day 8, tubes refed with 2 ml of fresh medium.

TABLE IV-E

Tissue Culture Purity Tests on the AGMK Cell Suspension -
Passage 17A, LOT #4889 at Approximately $5 \times 10^5$ Cells/ml
Whole Human Embryo Fibroblast Cells - (FL 5000) - (Passage 22, LOT #4842)

|  |  |  | Day 7 Results | | Day 14 Results | |
|---|---|---|---|---|---|---|
|  |  |  | AGMK | Controls | AGMK | Controls |
| 0.1% Guinea Pig RBC | at | 2°–8° C. | 0/2 | 0/2 | 0/2 | 0/2 |
|  | at | 35°–37° C. | 0/2 | 0/2 | 0/2 | 0/2 |
| 0.075% Chicken RBC | at | 2°–8° C. | 0/2 | 0/2 | 0/2 | 0/2 |
|  | at | 35°–37° C. | 0/2 | 0/2 | 0/2 | 0/2 |
| 0.1% Human RBC | at | 2°–8° C. | 0/2 | 0/2 | 0/2 | 0/2 |
|  | at | 35°–37° C. | 0/2 | 0/2 | 0/2 | 0/2 |
|  | Giemsa Stain |  |  |  | 0/4 | 0/4 |
| Coxsackie A-9 Virus Challenge* | at $10^{-3}$ |  |  |  | 2/2 | 2/2 |
|  | $10^{-4}$ |  |  |  | 2/2 | 2/2 |
|  | $10^{-5}$ |  |  |  | 2/2 | 2/2 |
|  | $10^{-6}$ |  |  |  | 1/2 | 1/2 |
|  | Unchallenged Controls |  |  |  | 0/1 | 0/1 |

*Coxsackie A-9 Challenge results based on a 4-day incubation at 36° C. Prior to challenge, tubes refed with 2 ml of fresh medium.

TABLE IV-F

Tissue Culture Purity Tests on the AGMK Cell Suspension -
Passage 17A, LOT #4755 at Approximately $5 \times 10^5$ Cells/ml
Human Carcinoma of the Larynx - H.Ep-2 - (Passage 397, LOT #4808)

|  |  |  | Day 7 Results | | Day 14 Results* | |
|---|---|---|---|---|---|---|
|  |  |  | AGMK | Controls | AGMK | Controls |
| 0.1% Guinea Pig RBC | at | 2°–8° C. | 0/3 | 0/3 | 0/4 | 0/4 |
|  | at | 35°–37° C. | 0/3 | 0/3 | 0/4 | 0/4 |
| 0.075% Chicken RBC | at | 2°–8° C. | 0/3 | 0/3 | 0/4 | 0/4 |
|  | at | 35°–37° C. | 0/3 | 0/3 | 0/4 | 0/4 |
| 0.1% Human RBC | at | 2°–8° C. | 0/3 | 0/3 | 0/4 | 0/4 |
|  | at | 35°–37° C. | 0/3 | 0/3 | 0/4 | 0/4 |
|  | Giemsa Stain |  |  |  | 0/7 | 0/7 |

*On day 10, tubes refed with 2 ml of fresh medium.

EXAMPLE 6

In Vivo Tests for the Detection of Viable Adventitious Microbial Agents

The following tests were performed employing cell suspensions derived from Passage 17A—(Lots #4706, #4742, #4755 and #4788). These assays were performed with inocula consisting of approximately $1 \times 10^7$ cells per ml suspended in the culture medium in which they were grown.

1. Tests in Animals a. Suckling Mouse Assay: A total of 10 newborn CD-1 mice randomized from different litters (10 per mother, less than 24 hours old) were inoculated intracerebrally (I.Cer.) with 0.01 ml and intraperitoneally (I.P.) with 0.1 ml of the cell suspension from Lot #4706. An additional randomized group of 10 sucklings was inoculated in a similar manner with the original culture medium. A randomized group of 10 sucklings was included as uninoculated controls. All sucklings were observed daily for 14 days for deaths and/or signs of illness or distress. On day 2, one (1) suckling from each of the inoculated groups was found missing and presumed cannibalized. There were no other deaths and none of the sucklings exhibited any signs of illness or distress over this initial 14 day observation period.

On the 14th day, single pools were prepared of the emulsified tissue (minus skin and viscera) of the following groups: (a) AGMK inoculated pups (n=9); (b) culture fluid inoculated pups (n=9); and (c) uninoculated controls (n=10). A blind passage into newborn CD-1 mice was made of each pool via the I.Cer. and I.P. routes: each pool into 10 newborns from mixed litters. An additional litter of 10 sucklings was included as uninoculated controls for this blind passage. All sucklings were observed daily for 14 days for deaths and/or signs of illness or distress. There were no deaths recorded for the AGMK or culture medium inoculated pups or for the uninoculated control group; however, on day 3, 4 sucklings were missing and presumed cannibalized in (c) the passaged control group. None of the sucklings exhibited any signs of illness or distress over this final 14 day observation period.

Because none of the AGMK cell suspension or culture medium inoculated sucklings exhibited any signs of a transmissible agent or of Coxsackie virus infection or of any viral infection, and because >90% of these inoculated sucklings (19 of 20) remained healthy and survived the entire observation period, this assay in suckling mice was considered satisfactory.

b. Adult Mouse Assay: Each of 20 adult CD-1 mice (VAF, 15–20 grams each) was inoculated I.Cer. and I.P. with 0.03 ml and 0.5 ml, respectively, with the cell suspension Lot #4788. An additional 5 mice were inoculated in a similar manner with the original culture medium. Four mice were included as uninoculated controls. Mice were observed daily for deaths and/or signs of illness or distress over a 21 day period. There were no deaths recorded and all mice survived the entire 21 day observation period with no evidence of lymphocytic choriomeningitis virus infection or any other viral infection. This test in adult mice was considered satisfactory.

c. Adult Guinea Pig Assay: Each of 5 Hartley strain guinea pigs (VAF, 350–450 grams each] was inoculated I.Cer. and I.P. with 0.1 ml and 5.0 ml, respectively, with the cell suspension Lot #4755. An additional guinea pig was inoculated in a similar manner with the original culture medium. One (1) guinea pig was included as an uninoculated control. All were observed daily for deaths and/or signs of illness or distress over a 6 week period; none were recorded. Commencing on day 21, daily rectal temperatures were taken with a digital thermometer and recorded (at approximately 0900 hours) for all guinea pigs until time of sacrifice. The average temperatures (° C.) for the AGMK inoculated guinea pigs were: 39.26, 39.30, 39.40, 39.46 and 39.53; for the medium inoculated guinea pig: 39.32; and for the control: 39.37. There were no significant temperature rises indicative of either bacterial or viral infection. All guinea pigs appeared healthy and survived the entire 42-day observation period at which time they were necropsied following euthanasia with Halothane and exsanguination. Inspection of the abdominal and thoracic cavities by the consulting veterinarian did not identify gross lesions or pathological changes. This assay in adult guinea pigs was considered satisfactory.

d. Adult Rabbit Assay: Each of 5 New Zealand white rabbits (1500–2500 gm each) was inoculated intradermally (I.D.) with 0.1 ml per each of 10 sites and subcutaneously (S.Q.) with 9.0 ml of the AGMK cell suspension Lot #4788. One (1) rabbit was similarly inoculated with the original culture medium. One (1) rabbit was included as an uninoculated control. Animals were observed daily for 28 days for deaths, illness, distress and/or lesions at the sites of inoculation. No deaths were recorded and all rabbits remained healthy without exhibiting any signs of illness or distress or lesions at the sites of inoculation. This test in adult rabbits was considered satisfactory. The results of these in vivo animal safety tests are summarized in Table V—A and B.

2. Tests in Embryonated Eggs

For these studies, specific pathogen-free embryonated eggs were obtained from SPAFAS, Inc., Reinholds, PA. These eggs came from Flock L061-E.

a. Allantoic Inoculation: Each of ten 10-day old embryonated eggs was inoculated via the allantoic route with 0.5 ml of the AGMK suspension Lot #4706. An additional 5 eggs were inoculated in a similar manner with the original culture medium. Five (5) eggs were included as uninoculated controls. Eggs were incubated at 36° C.±1° C. for 72 hours and then candled for deaths (1 of 5 medium inoculated) and chilled overnight at 2°–8° C. Allantoic fluids were harvested individually, incubated in a 37° C. water bath for 60 minutes to elute any adsorbed agent(s), and then clarified by centriflugation at 2500 rpm for 15 minutes at 20° C. Pools were prepared for each of the 3 sets of eggs employing equal volumes from each individual harvest. The pools were assayed for hemagglutination both undiluted and at a 1:10 dilution with incubation at 2°–8° C. and at room temperature (15°–+° C.) using the following erythrocytes in PBS at (pH 7.2): guinea pig at 0.6%; chick at 0.4%; and human at 0.6%. All fluids were negative for hemagglutination at both dilutions and at both temperatures with all 3 RBC suspensions.

The sample pools were subpassaged in 0.5 ml amounts into 10-day old embryonated eggs via the allantoic route as follows: the pool from the AGMK cell suspension into 10 eggs; the pool from the medium into 5 eggs; and the pool from the uninoculated eggs into 5 eggs. An additional 5 eggs were included as uninoculated controls. Eggs were incubated at 36° C.±1° C. for 72 hours and then candled for deaths (none recorded) and chilled overnight at 2°–8° C. Allantoic fluids were harvested, handled and tested as described above. All 4 pools were negative for hemagglutination at both dilutions and at both temperatures with all 3 RBC suspensions.

There were no deaths recorded for any of the eggs inoculated with the AGMK cell suspension. Since none of the harvest fluids exhibited any hemagglutination when tested against guinea pig, chick or human RBC, this aspect of the embryonated egg study was considered satisfactory.

b. Yolk Sac Inoculation: Each of ten 6-day old embryonated eggs was inoculated into the yolk sac with 0.5 ml of the AGMK cell suspension Lot #4742. Five (5) eggs were similarly inoculated with the original culture medium and 5 eggs were included as uninoculated controls. Eggs were incubated at 36° C. [±1° C.] for 9 days with periodic candling for deaths. Of the medium-inoculated eggs, 2 were found dead (1 each on days 2 & 5); and, of the AGMK-inoculated eggs, 2 were inadvertently broken. No other deaths or losses were recorded. Each group of yolk sacs (AGMK group=8; medium group=3; controls=5) was harvested, pooled, washed in PBS, emulsified by grinding and clarified by centrifugation at 2500 rpm for 20 minutes at 20° C.

The 3 clarified suspensions were subpassaged via the same route into fresh 6-day old embryonated eggs as follows: AGMK group into 10 eggs; medium group into 5 eggs; control group into 5 eggs. An additional 5 eggs were included as uninoculated controls. All eggs were incubated at 36° C.±1° C. for 9 days with periodic candling for deaths. On day 7, 3 eggs were found dead; 2 from the AGMK group and 1 from the medium group. There were no other deaths recorded.

This aspect of the embryonated egg study was considered satisfactory, because there was a greater than 80% overall survival (16 of 18) of embryonated eggs (primary and subpassage) inoculated with the AGMK cell suspension and viability of the egg was confirmed.

EXAMPLE 7

Use of the Characterized AGMK Cell Substrate for:
(1) Isolation and Growth of Human Rotaviruses:
and (2) Production of Live Vaccines Containing Such Viruses The AGMK cells are the only characterized cells tested to date that are suitable for vaccine purposes and support the efficient growth of completely homologous human rotaviruses, i.e., rotaviruses that derive each of their 11 gene segments from a human rotavirus. This is particularly important because a number of candidate homologous human rotavirus vaccine strains are now under development, including those shown in Table V.

As seen in Table V, two candidate human vaccine rotaviruses of G serotype 1 or G serotype 3 recovered from newborn infants were observed to grow to moderately high or high titer in AGMK cells, whereas, each of these neonatal rotavirus strains was markedly restricted in its capacity to grow in two types of cells certified for vaccine production, i.e., $FRhL_2$ or Vero cells. In addition, one of these neonatal rotavirus strains was also markedly restricted in replicative capacity in human fetal fibroblast cell strain MRC-5 which is licensed for vaccine production.

Similar observations were made with two cold-adapted (ca) mutants of human rotavirus of G serotype 1 or G serotype 2 that are also promising candidate live virus vaccine strains. Both human rotavirus mutants grew efficiently ire AGMK cells but were significantly or markedly restricted in their growth in certified cells $FRhL_2$ and Vero.

A. Isolation and Serial Passage of Neonatal Human Rotavirus Strains

Initially, the toxicity of each new preparation of purified trypsin is determined for the AGMK cells to be tested. A known positive stool extract is pre-treated with antibiotics (200 µg/ml gentamicin; 100 µg/ml neomycin; and 5 µg/ml fungizone) for 60 minutes at room temperature. Equal volumes of stool extract and trypsin at pre-determined concentration, e.g., 10 µg/ml, are mixed and allowed to incubate at 37° C. in a water bath for 30 minutes. In the interim, the cultures to be inoculated are washed three times with appropriate volumes (e.g., 3 ml for roller tubes, 10 ml for T25 flasks, 30 ml for T75 flasks and 100 ml T175 flasks) of serum-free medium to dilute the serum that had been in the growth medium in order to prevent components of serum from inactivating trypsin activity.

Roller tube cultures are inoculated with a 0.5 ml volume of the stool/trypsin mixture which is allowed to adsorb at 36° C.±1° C. for 60 minutes while rotating on a roller drum apparatus. Cultures are washed once and fed with 3 ml volumes of (EMEM) containing 1% of 10× SPG (sucrose, 2.18M; $KH_2PO_4$, 0.038M; $K_2HPO_4$, 0.072M; and monosodium glutamate, 0.054M) and 1 µg/ml trypsin. Cell cultures in which trypsin is omitted are also included to control for the effect of trypsin. Incubation is at 36° C.±1° C.

Cultures are examined microscopically on a daily basis and cultures are harvested when cytopathic effect (CPE) that involves 75 to 100% of the cells is evident. Virus and control cultures are treated similarly with 10% of 10× SPG (v/v) and subjected to one freeze-thaw cycle prior to harvest, sterility testing, distribution for storage, and serial passage. All subsequent passages are carried out either in roller tube cultures or in 25 $cm^2$ flask cultures employing similar procedures but with variation in trypsin concentration in both pre-treatment and in the final overlay.

An efficient system for producing virus plaques in AGMK cells is developed using methods that are routine in the art so that the virus can be plaque purified in order to obtain a homogeneous population of virus for subsequent vaccine development. The harvest fluids are routinely titrated in the simian MA-104 cells to measure the virus yield obtained. The virus is then triply-plaque-purified AGMK cells and the resulting clone is amplified by serial passage in progressively larger tissue culture vessels. The conditions for maximum yield based on trypsin concentration employed in both pretreatment and final overlay is determined for the progeny of the isolated clone using methods well known in the art.

B. Adaptation and Serial Passage Human Neonatal Rotaviruses or Other Human Rotavirus Strains The human rotaviruses exhibit a very narrow tissue culture host range. As a consequence, isolation and serial passage of various strains are usually performed in commercially available laboratory cell cultures such as simian MA-104 or primary monkey kidney, both of which are unsuitable for vaccine production. The former cells have not been validated as a substrate for vaccine production and the latter cells are notorious for their contamination with various simian microbial agents including retroviruses. In contrast to MA104 or primary monkey kidney cells, cell substrates certified for vaccine production, such as simian FRhL-2 or Vero cells, either fail to support growth of completely homologous human rotaviruses or allow only poor growth.

Many well characterized rotaviruses have been isolated, serially passaged and triply plaque-purified in commercially available laboratory cell culture systems not suitable for vaccine production. In those instances where it was necessary to use such viruses in vaccine development, the viruses were subsequently passaged and biologically cloned in a cell substrate certified for vaccine development and production. Ideally, virus to be used in vaccines should be isolated and passaged only in tissue culture cells certified to be acceptable for vaccine production. The AGMK cells of this invention meet this requirement because they support efficient growth of fully homologous human rotaviruses (Table V).

To develop a vaccine, routine studies are performed in flask cultures to determine the conditions for maximum yield including trypsin concentration required in both pretreatment and final overlay. Once adaptation of the vaccine virus to the AGMK cell substrate has been achieved, the virus harvest is treated with ether (1 part ether to 4 parts virus suspension for 60 minutes at room temperature followed by a 30 minute bubbling with $N_2$ to drive off ether) to eliminate any ether-sensitive virus(es) that may have been present in the original clinical specimen or acquired subsequently during passage in cell culture prior to initiation of vaccine development.

Live Virus Vaccine and/or Suspension Production

To produce vaccine, it is preferable also to prepare several backup pools of virus as follows:

1. Primary Seed Virus Pool

A pool of virus and serially passaged tissue culture control fluids supplemented with 10% of 10× SPG (v/v) are prepared and, after sterility is confirmed, and potency is determined, the fluids are distributed into small aliquots for storage at or below −70° C. to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG (v/v) is prepared. After sterility is confirmed, and potency determined, the fluids are distributed into small aliquots for storage at or below −70° C. to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG (v/v) is prepared. After sterility is confirmed, potency is determined, and identity is confirmed by both serology and electrophoretic pattern, the fluids are distributed into multi-sized aliquots with storage at or below −70° C. These pools serve as first level back-up to final production. These fluids are subjected to the Tissue Culture Purity (Safety) Testing simultaneously with the vaccine lot. Total volume may range from 500 ml to 1 liter.

4. Live Virus Vaccine Production

Volume to be produced is based on the number of doses and containers required plus a minimum of 400 ml of crude fluid for safety testing. In addition to the virus pool, the production of a small pool (200–400 ml) of the passaged tissue culture control fluid is recommended for subsequent safety testing together with the crude virus harvest. Culture vessel fluids supplemented with 10% of 10× SPG (v/v) are subjected to one (1) freeze-thaw cycle prior to individual harvest and sterility testing. A sample pool is prepared and assayed for potency. Identity is confirmed by both serology and electrophoretic pattern. The individual harvests are stored at or below −70° C. When sterility, potency and identity are confirmed, crude harvests are thawed and pooled. Samples of about 400 ml are removed for safety testing. The remainder of the fluid is clarified by centrifugation at 1200 g for 20 min. at 5° C., re-pooled, and distributed into final containers.

EXAMPLE 8

Adaptation of Human x Animal Reassortant Rotaviruses To Growth and Serial Passage in the Characterized AGMK Cell Substrate and the Use of Such Cells for Production of Live Virus Vaccines Live attenuated rotavirus vaccines can be made using reassortant rotaviruses that derive ten of their eleven gene segments from their animal rotavirus parent and only one gene segment from their human rotavirus parent (usually the gene that encodes the major protective antigen VP7). In one instance, human x rhesus monkey rotavirus reassortants are in a late stage of vaccine development and an application for a license has been submitted to the FDA.

All vaccine candidate human X animal reassortant rotaviruses studied to date have exhibited a very broad tissue culture host range attributable to the animal rotavirus parent, which contributes ten of its eleven gene segments to the reassortant. Although these vaccine candidate reassortants can proliferate to high titer in other cell lines certified for vaccine production, comparative studies with the AGMK cell substrate indicate that the AGMK cell substrate provided a significant advantage in viral growth yield over FRhL2 cells in every instance tested (Table V). In addition, the AGMK cell substrate has proved to be superior to Vero cells for the growth of human x rhesus rotavirus reassortants as well as rhesus rotavirus itself (Table V). In these instances, RRV and its human rotavirus reassortants grew in the AGMK cell line to a titer that was 16- to 100-fold higher than in FRhL2 cells and 10- to 1200-fold higher than in Vero cells (Table V). The only instances in which the AGMK cell substrate was not superior to Vero cells involved the human x bovine rotavirus reassortants where viral growth yield in the two cell lines was equivalent (Table V).

In addition to yield, the AGMK cell substrate has other advantages: (a) pre-treatment of virus with trypsin is not required; (b) the concentration of trypsin required in culture medium is reduced; (c) there is a significant reduction in the amount of virus required in the inoculum; (d) incubation time is shortened; and (e) the infected cell monolayer is completely lysed. Vaccine production is carried out as outlined above.

EXAMPLE 9

Adaptation of Human Astrovirus to Growth, Serial Passage and Subsequent Live Virus Vaccine Production in the Characterized AGMK Cell Substrate Previously, all human astroviruses have been isolated or propagated in cells inappropriate or unacceptable for vaccine production. A Type 2 strain of human astrovirus was successfully adapted to growth and serial passage in the AGMK cell substrate from seed virus grown in the simian LLCMK$_2$, cell line. Flask cultures of AGMK cell grown virus were studied to determine the optimal conditions for maximum yield based on trypsin concentrations employed in both pre-treatment and final overlay. Once adaptation was achieved, the virus harvest was treated with ether (1 part ether to 4 parts virus suspension for 60 minutes at room temperature followed by a 30 minute bubbling with $N_2$ to drive off ether) to eliminate any ether sensitive simian virus that may have been picked up during passage and plaquing in the commercially available laboratory cell culture systems. Fluid production was similar to that outlined for the human rotavirus.

EXAMPLE 10

Propagation of Live Attenuated Poliovirus Vaccine Strains in the Characterized AGMK Cell Substrate The Sabin live attenuated oral poliovirus vaccine strains were grown in the AGMK cells at passages 15 and 16. Each of the vaccine strains grew to high titer in AGMK cells (type 1 virus $10^{8.3}$TCID$_{50}$/ml, type 2 virus $10^{8.1}$TCID$_{50}$/ml, and type 3 virus $10^{8.6}$TCID$_{50}$/ml). These titers translate into 100 to 1000 vaccine doses per ml of. tissue culture harvest and are equivalent to the amount of virus produced by licensed primary AGMK cells and MRC-5 cells.

EXAMPLE 11

Isolation and/or Adaptation of Enteroviruses to Growth, Serial Passage and Subsequent Live Virus Suspension and/or Vaccine Production in the Characterized AGMK Cell Substrate Enteroviruses such as Coxsackie A9 virus were adapted to growth and serial passage in the characterized AGMK cells.

These cells are used to produce live virus suspensions and vaccine. Several seed virus pools have been produced.

Live Virus Vaccine and/or Suspension Production

1. Primary Seed Virus Pool

A pool of virus and serially passaged tissue culture control fluids supplemented with 10% of 10× SPG (v/v) are prepared and after sterility is confirmed and potency is determined, the fluids are distributed into small aliquots for storage at or below −70° C. to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG (v/v) are prepared. After sterility is confirmed, and potency determined, the fluids are distributed into small aliquots for storage at or below −70° C. to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG (v/v) are prepared. After sterility is confirmed, potency is determined, and identity confirmed by serology. The fluids are distributed into multi-sized aliquots with storage at or below ×70° C. These pools serve as first level back-up to final production. These fluids are subjected to the Tissue Culture Purity (Safety) Testing simultaneously with the vaccine lot. Total volume may range from 500 ml to 1 liter.

4. Live Virus Vaccine Production

Volume to be produced is based on the number of doses and containers needed plus a minimum of 400 ml of crude fluid for the required safety testing. In addition to the virus pool, the production of a small pool (200–400 ml) of the passaged tissue culture control fluid is recommended for subsequent safety testing together with the crude virus harvest. Culture vessel fluids supplemented with 10% of 10× SPG (v/v) are subjected to one (1) freeze-thaw cycle prior to individual harvest and sterility testing. A sample pool is prepared and assayed for potency and identity is confirmed by serology. The individual harvests are stored at or below −70° C. When sterility, potency and identity are confirmed, crude harvests are thawed and pooled. Samples of about 400 ml are removed for safety testing. The remainder of the fluid is clarified by centrifugation at 1200 g for 20 min. at 5° C., re-pooled. and distributed into final containers.

EXAMPLE 12

Isolation and Adaptation of Respiratory Syncytial Virus (ESV) to Growth and Serial Propagation in the Characterized AGMK Cell Substrate and Use of These Cells for Production of a Live Virus Vaccine Respiratory syncytial viruses, subgroup A and B types, have been readily isolated in these AGMK cell cultures directly from human nasal and/or throat secretions. Specimens are centrifuged at 3000 rpm for 10 minutes to remove any particulate matter and then treated with antibiotics (200 μg/ml gentamicin; 100 μg/ml neomycin; and 5 μg/ml fungizone) for 60 minutes at room temperature. The antibiotic-treated specimens are inoculated into roller tube cultures of the AGMK cells and incubated at 36° C.±1° C. on a roller drum. Once cytopathic effects are evident, cultures are harvested and further passages are carried out either in roller tubes or in flask cultures with subsequent serial passage and plaque purification. Subsequently, virus mutants are produced by chemical mutagenesis or are selected by passage at suboptimal temperature using the AGMK cells in either instance. Live virus vaccine is then prepared using the AGMK cells.

Final viral yield of candidate live attenuated RSV vaccine strains grown in the AGMK cells was greater than that of these viruses grown in Vero cells, which were previously the most efficient cell substrate certified for production of RSV vaccines. An example is seen in Table VI, where the virus yield of a cold-passaged, temperature sensitive mutant of RSV (designated RSV A2 cpts248/404) is shown to be 4- to 16-fold higher in the AGMK cell line than in Vero cells. Also, the amount of RSV produced by the human fetal diploid cell line MRC-5, which has been licensed for use in production of virus vaccines, is 10- to 100-fold less than in AGMK cells. This mutant is highly attenuated but still capable of inducing resistance to RSV in susceptible chimpanzees, which represent the most relevant animal surrogate for evaluation of attenuation and protective efficacy of RSV mutants prior to initiation of clinical trials in humans.

Live attenuated RSV vaccines are designed to be used in very young infants, the population at greatest risk of life-threatening RSV disease. Because of the need to immunize such young individuals, the live vaccine must be very attenuated (i.e., demonstrably weakened). Thus, it is noteworthy that the RSV A2 cpts248/404 mutant was able to attain a high titer in AGMK cells. Clearly, success of a vaccine containing this mutant and live RSV vaccines in general will require attainment of a high level of viral yield.

To produce live virus vaccine, conditions for good growth and viral yield, such as temperature of incubation and inoculum size, are determined by routine methods with production proceeding as follows:

Live Virus Vaccine and/or Suspension Production

1. Primary Seed Virus Pool

A pool of virus and serially passaged tissue culture control fluids supplemented with 10% of 10× SPG (v/v) are prepared and after sterility is confirmed and potency is determined, the fluids are distributed into small aliquots for storage at or below −70° C. to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG (v/v) is prepared. After sterility is confirmed, and potency determined, the fluids are distributed into small aliquots for storage at or below −70° C. to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG (v/v) are prepared. Sterility is confirmed, potency is determined, and identity confirmed by serology. The fluids are distributed into multi-sized aliquots with storage at or below −70° C. These pools serve as first level back-up to final production. These fluids are subjected to the Tissue Culture Purity (Safety) Testing simultaneously with the vaccine lot. Total volume may range from 500 ml to 1 liter.

4. Live Virus Vaccine Production

Volume to be produced is based on the number of doses and containers needed plus a minimum of 400 ml of crude fluid for the required safety testing. In addition to the virus pool, the production of a small pool (200–400 ml) of the passaged tissue culture control fluid is recommended for subsequent safety testing together with the crude virus harvest. Culture vessel fluids supplemented with 10% of 10× SPG (v/v) are harvested directly without undergoing a freeze—thaw cycle. A sample pool is prepared and assayed for potency and identity is confirmed by serology. The crude harvests are pooled and aliquots of about 400 ml are removed for safety testing. The remainder of the fluid is clarified by centrifugation at 1200 g for 20 min. at 5° C., re-pooled, and distributed into final containers.

EXAMPLE 13

Isolation and Adaptation of Parainfluenza Viruses to Growth and Serial Propagation in the Characterized AGMK Cell Substrate and Use of These Cells for Production of a Live Virus Vaccine Parainfluenza viruses types 1, 2 and 3 were isolated previously in primary AGMK cell cultures directly from human nasal and/or throat specimens. Subsequently, virus types 1, 2 and 3 were readily adapted to growth in the characterized AGMK cells. For isolation in the characterized AGMK cell substrate clinical specimens are centrifuged at 3000 rpm for 10 minutes to remove any particulate matter and then treated with antibiotics (200 µg/ml gentamicin; 100 µg/ml neomycin; and 5 µg/ml fuigizone) for 60 minutes at room temperature. The antibiotic-treated specimens are inoculated into the AGMK cell substrate roller tube cultures and incubated at 36° C.±1° C. on a roller drum. Once cytopathic effects and/or hemadsorption (with 0.1% guinea pig RBC in PBS, pH 7.2) is evident, cultures are harvested with further passages carried out either in roller tubes or in flask cultures with subsequent serial passage followed by plaque purification. Subsequently, virus mutants are produced by chemical mutagenesis or are selected by passage at suboptimal temperature, using the AGMK cell substrate in either instance.

An attenuated cold-adapted (ca) mutant of parainfluenza virus type 3 (designated PIV3 ca cold passage 45) was successfully grown to high titer in the AGMK cell substrate. Growth yield of the mutant was similar to the yield obtained in Vero cells, a certified simian cell line that has not yet been licensed for production of live virus vaccine for use in humans. However, as shown in Table VII, final viral yields in the AGMK cells were approximately 30-fold higher than in the commonly used, certified fetal rhesus lung cell strain, FRhL-2, which also has not been licensed as yet for production of human viral vaccines.

The PIV3 ca cold passage 45 mutant, which is now in Phase II clinical trials, is satisfactorily attenuated for young infants who have not been previously infected with naturally occurring PIV3. Although the mutant is very attenuated in young infants, it nonetheless stimulates production of protective levels of serum PIV3 antibodies. Based upon the results of clinical trials of the ca mutant in young infants, we calculate that 1 ml of the viral yield from infected AGMK cells contains 30 vaccine doses of PIV3 ca cold passage 45. Attainment of this level of viral growth during vaccine production is particularly noteworthy because the live PIV3 vaccine virus has been weakened so that is can be administered safely to infants and young children, the target population for immunization.

To produce live virus vaccine, conditions for good growth and viral yield, such as temperature of incubation and inoculum size, are determined by routine methods with production proceedings as follows:

Live Virus Vaccine and/or Suspension Production
1. Primary Seed Virus Pool

A pool of virus and serially passaged tissue culture control fluids supplemented with 10% of 10× SPG (v/v) are prepared and, after sterility is confirmed and potency is determined, the fluids are distributed into small aliquots for storage at or below −70° C. to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG (v/v) is prepared. After sterility is confirmed, and potency determined, the fluids are distributed into small aliquots for storage at or below −70° C. to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG (v/v) are prepared. Sterility is confirmed, potency is determined, and identity confirmed by serology. The fluids are distributed into multi-sized aliquots with storage at or below −70° C. These pools serve as first level back-up to final production. These fluids are subjected to the Tissue Culture Purity (Safety) Testing simultaneously with the vaccine lot. Total volume may range from 500 ml to 1 liter.

4. Live Virus Vaccine Production

Volume to be produced is based on the number of doses and containers needed plus a minimum of 400 ml of crude fluid for the required safety testing. In addition to the virus pool, the production of a small pool (200–400 ml) of the passaged tissue culture control fluid is recommended for subsequent safety testing together with the crude virus harvest. Culture vessel fluids supplemented with 10% of 10× SPG (v/v) are subjected to one (1) freeze-thaw cycle prior to individual harvest and sterility testing. A sample pool is prepared and assayed for potency and identity. The individual harvests are stored at or below −70° C. When sterility, potency and identity are confirmed, crude harvests are thawed and pooled. Samples of about 400 ml are removed for safety testing. The remainder of the fluid is clarified by centrifugation at 1200 g for 20 min. at 5° C., re-pooled, and distributed into final containers.

EXAMPLE 14

Isolation and/or Adaptation of Influenza Viruses to Growth in the Characterized AGMK Cell Substrate and Use of These Cells for Production of a Live or Inactivated Virus Vaccine Influenza viruses type A, subtypes H3N2, and H1N1 and type B, have been readily adapted to growth in this characterized AGMK cell line. A significant advantage of isolating and growing influenza viruses in a mammalian cell line rather than in embryonated chicken eggs stems from the fact that the hemagglutinin (the major protective viral protein of influenza virus) retains the same amino acid sequence and conformation as that present in a virus isolated from humans. In contrast, mutants bearing mutations affecting the hemagglutinin are selected during adaptation of virus to growth in eggs. These mutations confer upon the mutant a growth advantage in eggs.

The advantages of producing influenza virus vaccines, either live or killed, in a mammalian tissue culture system rather than in embryonated eggs derive from retention of the major protective antigenic sites on the influenza virus hemagglutinin (HA) when virus is grown in mammaliam tissue culture. Adaptation of influenza A or B virus to efficient growth in embryonated chicken eggs frequently results in selection of viral mutants that possess mutations affecting one of the major protective antigenic sites on the viral HA, Loss of such an HA epitope that induces protective antibodies diminishes the effectiveness of a vaccine containing this form of viral antigenic mutant. A number of studies have shown that influenza viruses isolated and propagated only in mammalian cell culture are more closely related antigenically to naturally circulating viruses than are egg-adapted influenza virus strains. For this reason it would be advantageous to isolate and maintain influenza A and B virus vaccine strains in a mammalian cell culture system, preferably primate, so as to maintain authentic antigenic structure of HA which is the major protective protein of these viruses.

As shown in Table VIII, a variety of influenza A viruses of subtype H1N1 or H3N2 grew efficiently in the AGMK cell substrate. Various influenza B virus strains also grow in the AGMK cells, albeit somewhat less well than the influenza A viruses. Since egg-propagated viruses were used as the inoculum in this experiment, the viral yields shown in Table VIII are minimal estimates because egg adaptation would be expected to select for mutants able to grow efficiently in eggs. Such mutants often grow less well in primate cells than the original naturally occurring virus as a consequence of the mutations responsible for egg adaptation.

The AGMK cells can be used to isolate influenza A and B viruses from infected humans and serve as a cell substrate for production of virus that is used to produce an inactivated vaccine. Alternatively, the AGMK cells can be used to isolate and propagate virus during the derivation of attenuated mutants that are used for formulation of a live attenuated virus vaccine.

EXAMPLE 15

Isolation and/or Adaptation of Human and Simian Hepatitis A Viruses to Growth, Serial Passage and Subsequent Live and Inactivated Virus Vaccine Production in the Characterized AGMK Cell Substrate Wild-type hepatitis A virus strains of human origin grow poorly or not at all in cell culture on primary isolation: they must be adapted to grow efficiently in cell culture by the laborious procedure of serial passage. In contrast, wild-type HAV of simian origin replicates moderately well during primary isolation in certain primate cells. However, certified or licensed cell culture systems suitable for primary isolation and adaptation of HAV strains of human or simian origin are not readily available or do not support the replication of HAV to high levels. Although the examples are for human HAV, it will be obvious to one skilled in the art that the techniques can be applied to HAV strains of simian origin.

Human hepatitis A virus, strain HM-175 (HAV/7). a strain suitable for a candidate live attenuated vaccine as well as a candidate inactivated vaccine, was compared for ability to replicate in AGMK cells, FRhK-4 (clone 11-1, the most sensitive cell line for replicating this virus to date), and licensed MRC-5 human diploid cells. Conditions for cell culture were those commonly used for the replication of HAV in FRhK-4 cells.

Figure 3:
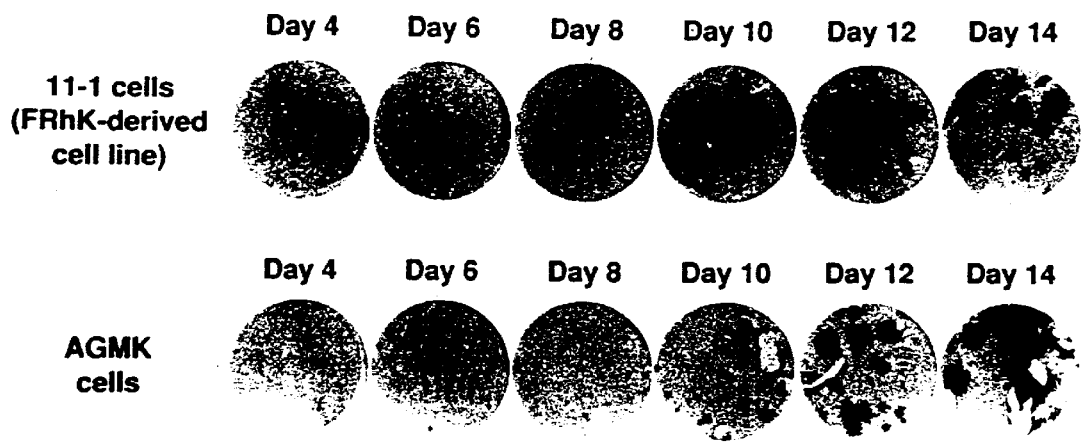
FIG. 3 depicts the results of a radioimmunofocus assay of HAV/7 as a fraction of time for plaque formation for 11-1 cell (FRhK-derived cell line) and for AGMK cells.

As seen in Table IX and FIG. 3, HAV replicated to the same titer and at the same rate in the AGMK cell substrate, which is suitable for vaccine development and production, as in FRhK-4, clone 11-1 cells, which are not suitable for vaccine development. Furthermore, the size of the HAV plaques, as measured by the radioimmunofocus assay, was the same in both cell types. In contrast, HAV strain HM-175 (HAV/7) did not replicate efficiently in MRC5 cells (a cell strain licensable for vaccine development) without extensive adaptation by serial passage.

Live Virus Vaccine and/or Suspension Production
1. Primary Seed Virus Pool

A pool of virus and serially passaged tissue culture control fluids supplemented with 10% of 10× SPG (v/v) are prepared and after sterility is confirmed and potency is determined, the fluids are distributed into small aliquots for storage at or below −70° C. to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG (v/v) are prepared. After sterility is confirmed and potency determined, the fluids are distributed into small aliquots for storage at or below −70° C. to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG (v/v) is prepared. Sterility is confirmed, potency is determined, and identity confirmed by serology. The fluids are distributed into multi-sized aliquots with storage at or below −70° C. These pools serve as first level back-up to final production. These fluids are subjected to the Tissue Culture Purity (Safety) Testing simultaneously with the vaccine lot. Total volume may range from 500 ml to 1 liter.

4. Live Virus Vaccine Production

Volume to be produced is based on the number of doses and containers needed plus a minimum of 400 ml of crude fluid for the required safety testing. In addition to the virus pool, the production of a small pool (200–400 ml) of the passaged tissue culture control fluid is recommended for subsequent safety testing together with the crude virus harvest. Culture vessel fluids supplemented with 10% of 10× SPG (v/v) are subjected to one (1) freeze-thaw cycle prior to individual harvest and sterility testing. A sample pool is prepared and assayed for potency and identity. The individual harvests are stored at or below −70° C. When sterility, potency and identity are confirmed, crude harvests are thawed and pooled. Samples of about 400 ml are removed for safety testing. The remainder of the fluid is clarified by centrifugation at 1200 g for 20 min. at 5° C., re-pooled, and distributed into final containers.

Inactivated Virus Vaccine and/or Suspension Production
1. Primary Seed Virus Pool A pool of virus and serially passaged tissue culture control fluids supplemented with 10% of 10× SPG [v/v] that are sterility confirmed, potency determined and distributed into small aliquots for storage at −70° C., or below, to serve as 3rd level back-up to final vaccine production. Total volume may range from 30 ml to 100 ml.

2. Secondary Seed Virus Pool

A pool of virus and serially passaged tissue culture control fluids supplemented with 10% of 10× SPG [v/v] that are sterility confirmed, potency determined and distributed into small aliquots with storage at −70° C., or below, to serve as 2nd level back-up to final vaccine production. Total volume may range from 100 ml to 300 ml.

3. Master Seed Virus Pool or Pre-Production Seed Virus Pool

A pool of virus and serially passaged tissue culture control fluids supplemented with 10% of 10× SPG [v/v] that are sterility confirmed, potency determined, identity confirmed, and distributed into multi-sized aliquots with storage at −70° C., or below. Pools serve as 1st level back-up to final production. Fluids to be subjected to the Tissue Culture Purity (Safety) Testing simultaneously with the vaccine lot. Total volume may range from 500 ml to 1 liter.

4. Inactivated Virus Vaccine Production

Volume to be produced is based on the number of doses and containers contracted for plus a minimum of 400 ml of crude fluid needed for the required safety testing. In addition to the virus pool, the production of a small pool [200–400 ml] of the passaged tissue culture control fluid is recommended for subsequent safety testing together with the crude virus harvest. Culture vessel fluids supplemented with 10% of 10× SPG [v/v] are subjected to one (1) freeze-thaw cycle prior to individual harvest and sterility testing. A sample pool is prepared and assayed for potency and identity and the individual harvests stored at −70° C., or below. When sterility, potency and identity are confirmed, crude harvests are thawed, pooled, clarified and purified before inactivation with formalin under standard conditions. The vaccine is then distributed into final containers and safety-tested for sterility.

The novel African Green Monkey Kidney cell line described, supra, was deposited with the American Type Culture Collection on Nov. 4, 1994, and accorded ATCC Designation No. CRL 11756. This deposit was made in accordance with the Budapest Treaty. This cell line will be irrevocably, and without restriction or condition, released to the public upon the issuance of a patent to this application.

TABLE V

Comparison of Growth Patterns of Candidate Rotavirus Vaccines in Various Cell Cultures

| Candidate Rotavirus Vaccine | Titer of Indicated Candidate Live Vaccine Virus Strain Produced in Indicated Cell Culture as Determined by Plaque Assay in MA104 Cells ($\log_{10}$pfu/ml)[a] | | | |
|---|---|---|---|---|
| Strain (Serotype)[b] | AGMK[c] | FRhL-2 | Vero[c] | MRC5[c] |
| Human Strains | | | | |
| D - ca30° C. (G1;P1A)[d] | 6.1 | No Growth | 4.7 | NT[e] |
| DS-1 - ca30° C. (G2;P1B)[d] | 6.3 | No Growth | No Growth | NT |
| M37 - neonatal (G1;P2) | 5.2 | No Growth | No Growth | NT |
| Neonatal (G3;P2) | 5.8 | Inconsistent, poor growth | Inconsistent, poor growth | No Growth |
| Human × Bovine Viral Reassortants[f] | | | | |
| D × UK(G1;P7) | 7.1 | 5.8 | 7.1 | NT |
| DS-1 × UK (G2;P7) | 7.3 | 5.3 | 7.0 | NT |
| P × UK-2 (G3;P7) | 7.0 | 5.4 | 6.9 | NT |
| ST-3 × UK-2 (G4;P7) | 7.2 | 5.8 | 6.6 | NT |
| Rhesus Rotavirus or Human × Rhesus Monkey Viral Reassortants[f] | | | | |
| D × RRV (G1;P5B) | 7.9[g] | 6.7 | 6.6[g] | NT |
|  | 7.9 |  | 5.7 |  |
|  | 8.3 |  | 5.1 |  |
| DS-1 × RRV (G2;P5B) | 7.6[g] | 5.7 | 6.6[g] | NT |
|  | 7.6 |  | 6.1 |  |
|  | 7.7 |  | 4.8 |  |
| RRV-2 (G3;P5B) | 8.5[g] | 6.7 | 7.2[g] | NT |
|  | 8.6 |  | 7.3 |  |
|  | 8.7 |  | 6.4 |  |
| ST3 × RRV (G4;P5B) | 7.6[g] | 6.1 | 6.3[g] | NT |
|  | 7.8 |  | 5.8 |  |
|  | 7.7 |  | 4.6 |  |

[a]Virus suspension grown in indicated cells.
[b]Serotype denotes viral outer capsid proteins (G and P) that induce protective neutralizing antibodies.
[c]AGMK = African green monkey kidney cells (derived from Cercopithecus ethiopus monkey); FRhL-2 = Fetal rhesus-lung cells; MRC5 = fibroblastic cells derived from fetal human lung. FRhL-2 and MRC5 are semi-continuous cell strains and can not be used beyond passage 32 for vaccine production; Vero is a continuous cell line; the number of times AGMK cells can be passaged serially and remain suitable for use in vaccine development has not been determined yet but is at least 16.
[d]Cold-adapted (ca) mutants of human rotavirus selected by growth and serial passage in cell culture at suboptimal temperature that does not allow efficient growth of naturally occurring (i.e., wild type) human rotavirus.
[e]NT = not tested.
[f]A single gene (encoding G serotype) derived from human rotavirus and all the remaining 10 genes derived from bovine or rhesus rotavirus.
[g]Growth yield from second passage in AGMK or Vero cells of virus previously passaged in FRhL-2 cells; values shown indicate growth yield from cell culture inoculated with 1:10; 1:00 or 1:1000 dilution of first passage material, respectively.
Note:
AGMK cells were used at passages 10, 11, 14 or 15.

TABLE VI

Efficient Replication of a Candidate Live Attenuated RSV Vaccine Strain (RSV A2 cpts248/404) in AGMK Substrate

| Vero Cell Grown RSV A2 cpts248/404 Used to Initiate Infection in | Quantity of Virus ($\log_{10}$pfu/ml) Produced in Cell Cultures Inoculated With* | |
|---|---|---|
|  | 1 ml | 5 ml |
| Vero Cells | 5.80 | 5.59 |
| AGMK Cells | 6.43 | 6.80 |

*RSV A2 cpts248/404 mutant grown and titrated at 32° C. Titrations performed in HEp2 cells at 32° C.
Note:
AGMK cells used at passages 14 and 15.

TABLE VII

Efficient Replication of a Candidate Live Attenuated Parainfluenza Virus Type 3 Vaccine Strain (PIV3 Cold-Adapted Cold Passage 45) in AGMK Cell Substrate

| Temperature of Incubation of PIV3 ca cp45 | Cell Substrate Used for Virus Growth[a] | Quantity of Virus Produced[b] ($\log_{10}$pfu/ml) | Hemagglutinin Titer (Reciprocal) |
|---|---|---|---|
| 32° C. | AGMK | 7.37 | 256 |
|  | Vero | 7.05 | 256 |
| 30° C. | AGMK | 7.49 | 256 |
|  | Vero | 7.22 | 128 |

TABLE VII-continued

Efficient Replication of a Candidate Live Attenuated Parainfluenza Virus Type 3 Vaccine Strain (PIV3 Cold-Adapted Cold Passage 45) in AGMK Cell Substrate

| Temperature of Incubation of PIV3 ca cp45 | Cell Substrate Used for Virus Growth[a] | Quantity of Virus Produced[b] ($Log_{10}$pfu/ml) | Hemagglutinin Titer (Reciprocal) |
|---|---|---|---|
| 26° C. | AGMK | 7.54 | 256 |
|  | Vero | 7.78 | 512 |

[a]Inoculum was FRhL2 cell grown virus currently being evaluated in clinical trials. The titer of this FRhL2 cell virus suspension was $10^{6.0}$ pfu/ml.
[b]Inoculated cell cultures harvested after 14 days of incubation except 32° C. AGMK cultures which were harvested at 7 days because of accelerated development of viral cell destructive effects.
Note:
AGMK cells used at passages 13 and 14.

TABLE VIII

Growth of Human Influenza A and B Viruses in AGMK Cell Substrate

| Type and Subtype | Virus Strain | Number of Passages in AGMK Cells at 36° C.[a] | Quantity of Virus Produced at the highest passage level as Determined by Titration in Indicated Cell Substrate | |
|---|---|---|---|---|
| | | | AGMK | MDCK[b] |
| A H3N2 | A/Wash/897/80 | 1 | 6.05 | 6.60 |
| | A/Korea/1/82 | 3 | 7.15 | 7.79 |
| | A/Bethesda/1/85 | 2 | 6.48 | 6.90 |
| | A/Los Angeles/2/87 | 3 | 7.16 | 7.76 |
| | A/Shandung/9/93 | 3 | 7.28 | 7.78 |
| A H1N1 | A/Texas/1/85 | 1 | 5.31 | 4.87 |
| | A/Kawasaki/9/86 | 3 | 6.50 | 6.81 |
| | A/Texas/36/91 | 1 | 5.23 | 6.04 |
| B | B/Texas/1/84 | 1 | <3.00 | 4.78 |
| | B/Ann Arbor/1/86 | 1 | 3.78 | 5.58 |
| | B/Victoria/2/87 | 1 | <3.00 | 4.82 |
| | B/Yamagata/16/86 | 1 | 4.41 | 5.72 |

[a]Passage in AGMK cell substrate initiated with egg grown influenza virus at a dilution of $10^{-3}$ or $10^{-4}$. The inoculum for passage in cell culture was also $10^{-3}$ or $10^{-4}$ (except B/Victoria/2/87 which was $10^{-2}$) in order to minimize generation of defective, interfering virus particles. Tissue culture medium and agarose overlay in plaque assays contained 0.5 µg/ml of trypsin.
[b]MDCK is a continuous cell line of canine kidney cells often used for titration of human influenza viruses.

TABLE IX

Ability of AGMK Cells to Support Efficient Growth and Plaque Formation of Candidate Hepatitis A Virus Vaccine Strain HM-175 (HAV/7)*

| | Cell Culture Used for Virus Replication | | |
|---|---|---|---|
| HAV Property | AGMK[a] | FRhK-4(11-1)[a] | MRC-5[a] |
| Titer ($log_{10}$pfu/ml) of Virus Achieved in Inoculated Culture[b] | 7.4 | 7.4 | Little or No Growth[c] |
| Plaque Size | Large | Large | — |

*Candidate strain for both inactivated and live attenuated HAV vaccines.
[a]AGMK = African green monkey kidney derived from Freeze #2129. FRhK-4(11-1) = HAV-permissive cell clone derived from fetal rhesus kidney-4 cells (Funkhouser AW, Purcell RH, D'Hondt E, Emerson SU, Attenuated hepatitis A virus: Genetic determinants of adaptation to growth in MRC-5 cells. J Virol 68:148–157; 1994). MRC-5 = fetal human lung fibroblast cell substrate.
[b]Determined by plaque assay on AGMK and FRhKA(11-1) cells.
[c]Growth not detected by plaque assay performed with FRhK-4(11-1) cell culture.
Note:
AGMK cells used at passages 12, 13, 15 and 16.

What is claimed is the following:

1. A method for producing a virus selected from the group consisting of rotaviruses, enteroviruses, polioviruses, respiratory viruses, astroviruses, and hepatitis A viruses, using a cell line originating from the kidney of an African Green Monkey, wherein said cell line supports the growth of rotaviruses, enteroviruses, polioviruses, respiratory viruses, astroviruses, and hepatitis A viruses, and wherein said cell line is substantially free of viable adventitious microbial agents, said method comprising the steps of:

1. inoculating said cell line with a sample containing an inoculum of said virus;
2. incubating said inoculated cell line to permit proliferation of said virus; and
3. harvesting the virus resulting from step 2.

2. A method, according to claim 1, wherein the virus is a human rotavirus.

3. A method according to claim 1, wherein said virus is a human X animal rotavirus reassortant.

4. A method, according to claim 1, wherein the virus is a human astrovirus.

5. A method, according to claim 1, wherein the virus is an enterovirus.

6. A method according to claim 1, wherein the virus is a Sabin live attenuated oral polio virus vaccine strain.

7. A method, according to claim 1, wherein the virus is a respiratory virus.

8. A method, according to claim 1, wherein the virus is a hepatitis A virus.

* * * * *